US007595152B2

(12) United States Patent
Lu et al.

(10) Patent No.: US 7,595,152 B2

(45) **Date of Patent: *Sep. 29, 2009**

(54) DETECTION OF INFLUENZA VIRUS

(75) Inventors: Peter S. Lu, Palo Alto, CA (US); Michael P. Belmares, San Jose, CA (US); Dave Garman, San Jose, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/698,798

(22) Filed: Jan. 26, 2007

(65) Prior Publication Data

US 2007/0224594 A1 Sep. 27, 2007

Related U.S. Application Data

(63) Continuation-in-part of application No. PCT/US2006/041748, filed on Oct. 21, 2006, and a continuation-in-part of application No. 11/481,411, filed on Jul. 3, 2006.

(60) Provisional application No. 60/792,274, filed on Apr. 14, 2006, provisional application No. 60/765,292, filed on Feb. 2, 2006, provisional application No. 60/726,377, filed on Oct. 13, 2005, provisional application No. 60/696,221, filed on Jul. 1, 2005.

(51) Int. Cl.

| | |
|---|---|
| ***C12Q 1/70*** | (2006.01) |
| ***G01N 33/53*** | (2006.01) |
| ***G01N 33/542*** | (2006.01) |
| ***G01N 33/00*** | (2006.01) |
| *C12M 1/34* | (2006.01) |

(52) U.S. Cl. ............................ 435/5; 435/7.1; 435/7.9; 435/7.92; 435/287.1

(58) Field of Classification Search ....................... None
See application file for complete search history.

(56) References Cited

U.S. PATENT DOCUMENTS

| | | | |
|---|---|---|---|
| 2003/0119203 | A1 | 6/2003 | Wei |
| 2005/0282743 | A1 | 12/2005 | Lu et al. |

FOREIGN PATENT DOCUMENTS

| | | |
|---|---|---|
| EP | 0 726 316 A2 | 8/1996 |

(Continued)

OTHER PUBLICATIONS

Dundon, et al. Progressive truncation of the Non-Structural 1 gene of H7N1 avian influenza viruses following extensive circulation in poultry. Virus Research 119 (2006) 171-176.*

(Continued)

*Primary Examiner*—Mary E Mosher
*Assistant Examiner*—Stuart W Snyder
(74) *Attorney, Agent, or Firm*—Townsend and Townsend and Crew, LLP

(57) ABSTRACT

The present application describes methods for detecting influenza A and/or influenza B and/or distinguishing between pathogenic and seasonal influenza A subtypes. Many of these preferred formats employ pan-specific antibodies (i.e., that react with all or at least multiple strains within an influenza type) to detect presence of influenza A and/or influenza B and PDZ domains in combination with panspecific antibodies to influenza A to distinguish pathogenic and seasonal influenza A subtypes.

21 Claims, 15 Drawing Sheets

FOREIGN PATENT DOCUMENTS

| | | | |
|---|---|---|---|
| EP | 0 293 184 | A2 | 11/1998 |
| JP | 2006-067979 | A | 3/2006 |
| JP | 2006 067979 | A | 3/2006 |

OTHER PUBLICATIONS

Songyang, et al. Recognition of Unique Carboxyl-Terminal Motifs by Distinct PDZ Domains. Science 275, 73 (1997); 73-77.*

Birch-Machin, et al. Expression of the nonstructural protein NS1 of equine influenza A virus: Detection of Anti-NS1 antibody in post infection equine sera. Journal of Virological Methods 65 (1997) 255-263.*

Rozek, et al. Evaluation of Immunological Status of Horses Against Influenza Virus Based on the Presence of Antibodies Against NS1 and M1 Proteins. Bull. Vet. Inst. Pulawy 47, 315-324, 2003.*

Basler, et al. Sequence of the 1918 pandemic influenza virus nonstructural gene (NS) segment and characterization of recombinant viruses bearing the 1918 NS genes. PNAS 2001; 98(5):2746-2751.*

Lipatov, et al. Neurovirulence in Mice of H5N1 Influenza Virus Genotypes Isolated from Hong Kong Poultry in 2001. Journal of Virology, 2003; 77(6):3816-3823.*

Jackson, et al. A new influenza virus virulence determinant: the NS1 protein four C-terminal residues modulate pathogenicity. Proc Natl Acad Sci U S A. Mar. 18, 2008;105(11):4381-6.*

Cheng, et al. Genetic analysis of NS1 fragment of human H5N1 influenza virus isolated in Anhui province and its expression in *Escherichia coli*. Wei Sheng Wu Xue Bao. Jun. 4, 2007;47(3):418-22. Abstract Only.*

Bezprozvanny, I., et al., "Classification of PDZ domains," *FEBS Letters*, 2001, 509: 457-462.

Binns, M. M., et al., "Genetic and antigenetic analysis of an equine influenza H3 isolate from the 1989 epidemic," *Archives of Virology*, 1993, 130: 33-43.

Brown, L. E., et al., "Antigenic Variation in the Influenza A Virus Nonstructural Protein, NS1," *Virology*, 1983, 130:134-143.

Burrows, R., "Laboratory Diagnosis of Some Virus Infections of the Upper Respiratory Tract of the Horse," *Equine Vet J.*, 1968, 1, 32-38.

Dimmock, N. J., "New Virus-Specific Antigens in Cells Infected with Influenza Virus," 1969, *Virology*, 1969, 39:224-234.

Lazarowitz, S. G., et al., "Influenza Virus Structural and Nonstructural Proteins in Infected Cells and Their Plasma Membranes," *Virology*, 1971, 46: 830-843.

Lin, D., et al., "Structure and Function of the NS1 Protein of Influenza A Virus," *Acta Biochimica et Biophysica Sinica*, Mar. 2007, 39(3):155-162.

Marion, R.M., et al., "Influenza virus NS1 protein interacts with viral transcription-replication complexes in vivo," *Journal of General Virology*, 1997, 78:2447-2451.

Marion, R.M.,et al., "The N-terminal half of the influenza virus NS1 protein is sufficient to nuclear retention of mRNA and ehancement of viral nRNA translation," *Nucleic Acids Research*, 1997, 25(21): 4271-4277.

Nakijima, K., et al., "Evolution of the NS Genes of the Influenza A Viruses. I. The Genetic Relatedness of the NS Genes of Animal Influenza Viruses," 1990, *Genes* 4:1, 5-13.

Newby, C., et al., "The RNA Binding Domain of Influenza A Virus NS1 Protein Affects Secretion of Tumor Necrosis Factor Alpha, Interleukin-6, and Interferon in Primary Murine Trachael Epithelial Cells," *Journal of Virology*, 81(17):9469-9480.

Obernauer, J., et al., "Large-Scale Sequence Analysis of Avian Influenza Isolates," *Science*, Mar. 17, 2006, 311: 1576-1580.

Satterly, N., et al., "Influenza virus targets the mRNA export machinery and the nuclear pore complex," *PNAS*, Feb. 6, 2007, 104(6)1853-1858.

Shaw, M. W., et al., "Immunologic studies on the influenza A virus nonstructural protein NS1," *Journal of Experimental Medicine*, 1982, 156:243-254.

Wolff, T. et al., "NS1-Binding Protein (NS1-BP): a Novel Human Protein That Interacts with the Influenza A Virus Nonstructural NS1 Protein Is Relocalized in the Nuclei of Infected Cells," *Journal of Virology*, Sep. 1998, pp. 7170-7180.

Zezula, J., et al., "The $A_{2A}$-adenosine receptor: a GPCR with unique features?" *British Journal of Pharmacology*, 2008, 153:S184-S190.

Zhang, Y., et al., "Structures of a Human Papillomavirus (HPV) E6 Polypeptide Bound to MAGUK Proteins: Mechanism of Targeting Tumor Suppressors bya High-Risk HPV Oncoprotein," *Journal of Virology*, Apr. 2007, 81(7):3618-3626.

Nakajima, K., et al., "Evolution of the NS Genes of the Influenza A Viruses II Characteristics of the Amino Acid Changes in the NS1 Proteins of the Influenza A Viruses", *Virus Genes*, 1990, vol. 4, No. 1, pp. 15-26.

Obenauer, John C., et al., "Large-Scale Sequence Analysis of Avian Influenza Isolates", *Science*, Mar. 17, 2006, vol. 311, pp. 1576-1580.

Ozaki, H., et al., "Detection of antibodies to the nonstructural protein (NS1) of influenza A virus allows distinction between vaccinated and infected horses", *Veterinary Microbiology*, Sep. 20, 2001, vol. 82, No. 2, pp. 111-119.

Ozaki, H., "A Rapid and Highly Sensitive Method for Diagnosis of Equine Influenza by Antigen Detection Using Immino-PCR", *Jpn. J. Vet. Res.*, 48 (4) 187-195 (2001).

Shaw, M. W., et al., "Immunologic Studies on the Influenza A Virus Nonstructural Protein NS1", *Journal of Experimental Medicine*, Jul. 1982, vol. 156, pp. 243-254.

Songyang, Z., et al., "Recognition of Unique Carboxyl-Terminal Motifs by Distinct PDZ Domains", *Science*, Jan. 3, 1997, vol. 275, pp. 73-77.

Tumpey, Terrence M., et al., "Diagnostic Approach for Differentiating Infected from Vaccinated Poultry on the Basis of Antibodies to NS1, the Nonstructural Protein of Influenza A Virus", *Journal of Clinical Microbiology*, Feb. 2005, vol. 43, No. 2, pp. 676-683.

PCT International Preliminary Report on Patentabiligy and Written Opinion of Jan. 10, 2008 for application No. PCT/US2006/026155.

U.S. Appl. No. 10/847,818 no published date, Peter S. Lu.

Non-Final Office Action mailed Aug. 30, 2006 in U.S. Appl. No. 10/847,818.

Response to Non-Final Office Action filed Jul. 5, 2007 in U.S. Appl. No. 10/847,818 (redacted).

Final Office Action mailed Jul. 27, 2007 in U.S. Appl. No. 10/847,818.

Response to Office Action filed Oct. 30, 2007 in U.S. Appl. No. 10/847,818 (redacted).

* cited by examiner

MXXXXXXXFQVXCFLWXXRKXXXXXXXXDXPFXDRXXRXXXXXXGRXXTXXXX
IXXXXXXGXXIXXXXXXXXXXXXXXXXXXSXXXXXYXXXMXXXXXXXXXXXXX
XXXXXXXXXXXXXDQXXXXKXXXLXXXXXXXXXXXXXXXLXRXXXXXXXXXXG
XXXXXXXXXXXXXXXXXXXXXXXXXXXEXXXXXXXXXXXXXXXXXXXXXXEXX
XXXXXXXXXXXXXXXXXX

FIG. 1A

XXXXXXXXXXXXXXXXXVXXRFXDXEXGXAXXXXXXXXXQXXXXXXXXXXGLD
XXXXXXXXXXXXEXXXEXXXDXXXXXXIAXVXXXXXLXXXXLXXXXXXXXXXX
XXXXXXXSXXXXMXXXIMXXXXXXXXXXXXXXXXXXXXXXXXXXXXXXXXRXX
XXXXXXXXXXXXXXXXXXXXXXXXXXXXXXXXXXXENXXXXXXXXXXXXXXXX
XXXXXXXXXXXRXXE (S/P) EV

FIG. 1B

MDSNTVLSFQVDCFLWHVRKRFADQELGDAPFLDRLRRDQKSLRGRGNTLGLDIETATRAGK
QIVERILEEESDEALKMTIASVPASRYLTDMTLEEMSRDWFMLMPKQKVAGSLCIKMDQAIM
DKTIILKANFSVIFDRLETLILLRAFTEEGAIRVGEISPLPSLPGHTGEDVKNAIGVLIGGL
EWNDNTVRVSENTIQRFAWRGSDEDGRLPFPPNQKRKMARTIESEVEK

FIG. 2

MADNMTTTQIEVGPGATNATINFEAGILECYERLSWQRALDYPGQDRLNRLKRKLESRIKTH
NKSEPESKRMSLEERKAIGVKMMKVLLFMDPSAGIEGFEPYCMKNPSNSNCPKCNWADYPLT
PGKCLDDIEEEPEDVDDPTEIVLRDMNNKDARQKIKEEVNTQKEGKFRLTIKRDIRNVLSLR
VLVNGTFLKHPNGYKSLLTLHRLNAYDQSGRLVAKLVATDDLTVEDEEDGHRILNSLFERFN
EGHPKPIRAAETAMGVLSQFGQEHRLSPEEGDN

FIG. 3

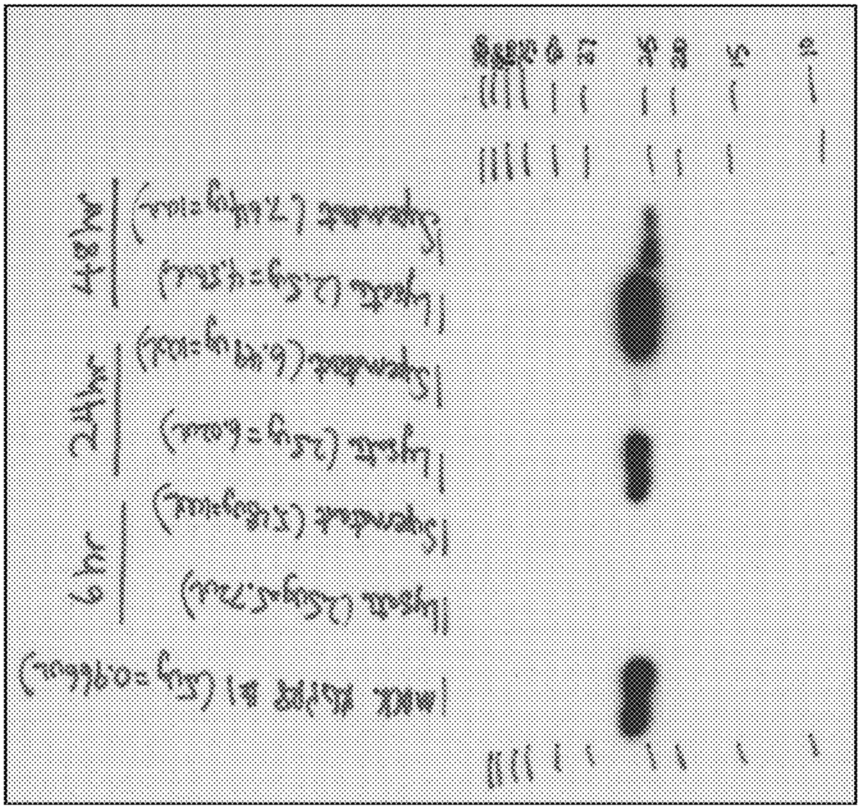
ECL+, 3min
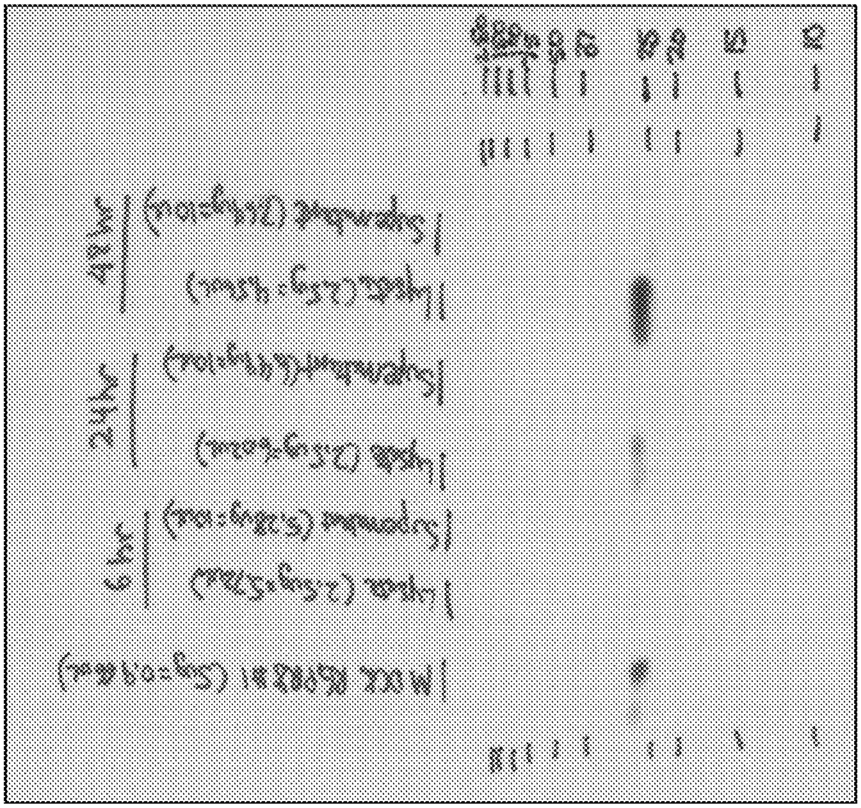
ECL+, 1sec
FIG. 5

Sample 1 (+)
In saline

Sample 2 (+)
In saline

Sample 3 (+)
In saline

Avian Flu Test
In 80% M4 media, 20% buffer B3

Pan-Flu A Test
In 80% M4 media, 20% buffer B3

Sample 12 (-)
In M4 media

Sample 9 (+)
In M4 media

Sample 7 (+)
In M4 media

|          | F89-1F4 | F89-2A10 | F89-2F3 | F89-2H2 | F89-4D5 | F89-4G12 |
|----------|---------|----------|---------|---------|---------|----------|
| Detector | ☺       | ✗        | ✗       | ✗       | ☺       | ☺        |
| Capture  | ☺       | ✗        | ✗       | ✗       | ☺       | ☺        |

|          | F89-7H10 | F94-4C10 | F94-1F8 | F94-3A1 | F94-1F9 | F94-5E5 |
|----------|----------|----------|---------|---------|---------|---------|
| Detector | ✗        | ☺ +      | ✗       | ☺       | ✗       | ✗       |
| Capture  | ✗        | ✗        | ☺ *     | ☺       | ☺ *     | ☺ *     |

\* With influenza 522    + With influenza 523

DETECTION OF INFLUENZA VIRUS

CROSS-REFERENCES TO RELATED APPLICATIONS

The present application is a continuation-in-part of PCT/US06/41748 filed Oct. 21, 2006, incorporated by reference in its entirety for all purposes. The present application is also a continuation in part of U.S. Ser. No. 11/481,411, an application claiming benefit under 35 USC 119(e) of 60/792,274, filed Apr. 14, 2006, 60/765,292, filed Feb. 2, 2006, 60/726,377, filed Oct. 13, 2005; and 60/696,221, filed Jul. 1, 2005, each of which is incorporated by reference in its entirety for all purposes.

BACKGROUND OF THE INVENTION

Influenza is caused by an RNA virus of the orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza type C viruses also infect only humans. They infect most people when they are young and rarely causes serious illness.

Current rapid immunodiagnostic tests for influenza antigens like "BINAX NOW FLU A and FLU B™" (Binax, Inc., Portland, Me), "DIRECTIGEN FLU A+B™" (Becton Dickinson, Franklin Lakes, N.J.), "FLU OIA™" (Biostar Inc., Boulder, Colo.), "QUICK VUE™" (Quidel, San Diego, Calif.), "INFLU AB QUICK©" (Denka Sieken Co., Ltd., Japan) and "XPECT FLU A & B" (Remel Inc., Lenexa, Kans.), can reportedly either detect influenza A or distinguish between influenza A and B. The complexity of the test formats may require special training. In addition, significant amounts of virion particles are commonly required to obtain a positive test result, limiting their use to a short window of time when virus shedding is at its highest levels. Assay sensitivity is also variable with up to 20% false negative test results in certain assays being of significant current concern (e.g., see "WHO recommendations on the use of rapid testing for influenza diagnosis," July 2005). Reverse-transcriptase PCR-based diagnostics (RT-PCR) has resulted in advances in capabilities, but is laborious and requires highly trained personnel making on-site or field-testing difficult. Because of the relative inefficiency of the reverse transcriptase enzyme, significant amounts of virus (e.g., $10^4$ virion particles) and as many as 20 primers may be required effectively to detect viral RNA. Unfortunately, RT PCR is not easily adapted to high throughput screening of subjects in an epidemic setting or to field uses in an agricultural or point-of-care setting.

Additionally, the complexity, diversity and rapid emergence of new influenza strains has made diagnosis of high risk strains difficult, and therefore rapid response is at present nearly impossible. For epidemiologists, diversity resulting from high mutation rates and genetic reassortment make it difficult to anticipate where new strains may originate and respond with the timely introduction of new diagnostic primers for PCR. As a result, (at present) the diversity of influenza dictates the necessity of multiplex PCR approaches.

BRIEF SUMMARY OF THE INVENTION

The invention provides method of detecting influenza A. The methods involve contacting a sample from a subject with a PDZ domain that specifically binds to a PL of an NS1 protein of a pathogenic strain of influenza A; detecting presence or absence of specific binding of the PDZ domain to the NS1 protein of pathogenic influenza A in the sample to determine presence or absence of the pathogenic influenza A in the sample; contacting the patient sample with a PDZ domain that specifically binds to a PL of an NS1 protein of a seasonal subtype influenza A; and detecting presence or absence of specific binding of the PDZ domain to the NS1 protein of the seasonal subtype influenza A to determine presence or absence of the seasonal subtype influenza A in the sample.

Optionally, the PDZ domain that specifically binds to the PL of an NS1 protein of pathogenic influenza A is a PSD95 domain. Optionally, the PDZ domain that specifically binds to the PL of an NS1 protein of a seasonal subtype influenza A is an INADL domain 8. Optionally, the sample is an orally obtained sample. Optionally, the subject is a human showing symptoms of influenza. Optionally, the specific binding of the PSD95 PDZ domain to the NS1 protein is detected by a sandwich assay in which the sample is contacted with an antibody that binds to the NS1 protein, and a complex of the PSD95 PDZ domain and the antibody both specifically bound to the NS1 protein is detected. Optionally, the specific binding of the INADL PDZ domain to the NS1 protein is detected by a sandwich assay in which a complex of the INADL PDZ domain and the antibody both specifically bound to the NS1 protein is detected. Optionally, the at least one PDZ domain of PSD95 comprises a PDZ domain 2 of PSD95. Optionally, the at least one PDZ domain comprises at least three copies of PSD95 domain 2. Optionally, the at least one PDZ domain comprises domains 1, 2 and 3 of PSD95. Optionally, the at least one PDZ domain of INADL comprises domain 8 of INADL. Optionally, the at least one PDZ domain of INADL comprises three copies of domain 8 of INADL.

The invention further provides methods of detecting influenza A. The methods involve contacting a sample from a subject with first and second pan specific antibodies that bind to different epitopes of an NS1 protein of influenza A; detecting presence or absence of a complex between the first and second antibodies and the NS1 protein to indicate presence or absence of influenza A. Optionally, the first and second antibodies each bind to an epitope within residues 8-21, 9-20, 29-38 or 45-49 of FIG. 1A. Optionally, the first and second antibodies compete with different antibodies selected from the group consisting of F64 3H3, F68 8E6, F64 6G12, F68 10A5, F80 7E8, F80 8F6, F80 9B1, F81 1C12, F81 1F3, F81 4D5, and F64 1A10.

The invention further provides a method of detecting influenza A. The method involves contacting a sample from a subject with at least one PDZ domain and at least one pan-specific antibody that binds to the NS1 protein of influenza A; detecting presence or absence of the NS1 protein of influenza A in the sample from presence of absence of a complex of the at least one PDZ domain and pan-specific antibody specifically bound to the NS1 protein. Optionally, the pan-specific antibody is a capture antibody immobilized to a solid phase. Optionally, the pan-specific antibody is a detection antibody. Optionally, the pan-specific antibody specifically binds to an epitope of the NS1 protein with residues 9-20, 29-38 or 45-49 of FIG. 1A. Optionally, the pan specific antibody is a monoclonal. Optionally, the pan specific antibody is a mixture of two monoclonals. Optionally, the pan specific antibody is a monoclonal antibody that competes with an antibody selected from the group consisting of F64 3H3, F68 8E6, F64 6G12, F68 10A5, F80 7E8, F80 8F6, F80 9B1, F81 1C12, F81 1F3, F81 4D5, and F64 1A10 for specific binding to an NS1 protein. Optionally, the patient sample is contacted with at least two PDZ domains attached to different regions of a support. Optionally, the at least two PDZ domains are a PSD95 domain and an INADL domain.

The invention further provides a method of detecting influenza B. The method involves contacting a sample with first and second pan specific antibodies that bind to different epitopes of an NS1 protein of influenza B; detecting presence or absence of a complex between the first and second antibodies and the NS1 protein to indicate presence or absence of influenza B. Optionally, the first and second antibodies each bind to an epitope within residues 10-28, 40-45, 50-57, 67-74, 84-100, 154-159, 169-173, 185-191, 212-224, 226-240 of FIG. 2. Optionally, the first and second antibodies compete with different antibodies selected from the group consisting of F89 1F4, F94 3A1, and F89-1F8.

The invention further provides methods of detecting influenza. The methods comprise contacting a sample from a subject with first and second pan-specific antibodies binding to different epitopes of an influenza B NS1 protein and first and second pan-specific antibodies binding to different epitopes of an influenza A NS1 protein; determining presence or absence of a complex formed between the influenza B NS1 protein and the first and specific pan-specific antibodies binding to it to indicate presence or absence of influenza B in the sample and determining presence or absence of a complex formed between the influenza A NS1 protein and the first and second pan-specific antibodies binding to it to indicate presence or absence of influenza A in the sample. Optionally, the methods further comprise contacting the patient sample with a PDZ domain specific for a PL of an NS1 protein from a pathogenic strain of influenza A; and detecting presence or absence of specific binding of the PDZ domain to the NS1 protein of the pathogenic strain of influenza A to indicate presence or absence of the pathogenic strain of influenza A. Optionally, the first and second pan-specific antibodies for influenza A are capture and detection antibodies respectively, and the presence of specific binding of the PDZ domain to the NS1 protein is detected by detecting a complex formed between the PDZ domain, the NS1 protein and the detection antibody. Optionally, the methods further comprise contacting the patient sample with a PDZ domain specific for a PL of an NS1 protein of a seasonal subtype of influenza A; and detecting presence or absence of specific binding of the PDZ domain to the NS1 protein of the seasonal subtype of influenza A to indicate presence or absence of the seasonal subtype of influenza A.

BRIEF DESCRIPTION OF THE DRAWINGS

FIG. 1A (SEQ ID NO:1) shows the invariant amino acid residues between NS1 proteins from three subtypes of influenza A, H1N1, H3N2 and H5N1. As described below, segments of NS1 protein including clusters of invariant amino acid residues are useful for inducing pan-specific antibodies.

FIG. 1B (SEQ ID NO:2) shows amino acid residues found in the NS1 protein of H5N1 but not found in H3N2 or H1N1. Clusters of these residues particularly the clusters at positions 21-28 and at the C-terminus are useful for preparing an antibody that binds to H5N1 without binding to the other two subtypes.

FIG. 2 (SEQ ID NO:3) shows a consensus sequence of residues of the NS1 protein from different strains of influenza A.

FIG. 3 (SEQ ID NO:4) shows a consensus sequence of residues of the NS1 protein form different strains of influenza B. Underlined residues are invariable between different strains.

FIG. 5 shows NS1 expression in MDCK cells infected with A/PR/8/34.

DEFINITIONS

Figure 4:
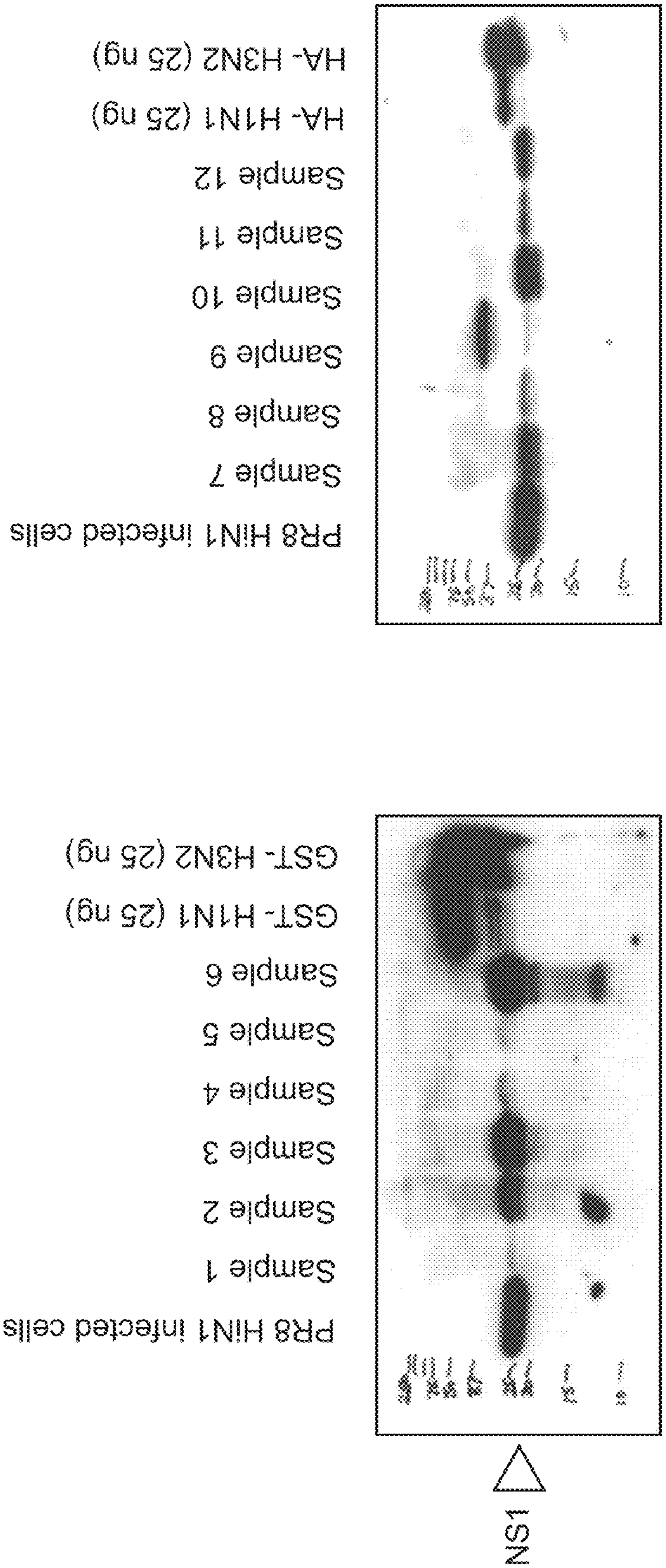
FIG. 4 shows the results of testing nasal secretions from six human Flu A positive samples.

"Avian influenza A" means an influenza A subtype that infects an avian subject and is transmissible between avian subjects. Representative examples of avian influenza hemagglutinin subtypes include H5, H6, H7, H9 and H10 and representative strains include H5N1, H6N2, H7N3, H7N7, H9N2, H10N4 and H10N5. Some strains of Avian influenza can also infect humans.

"Avian subject" means a subject suitable for testing or treatment including all species of birds, including both wild birds (such as wildfowl) and domesticated species (such as poultry). Preferably, the avian subject to be tested or treated is selected from the group consisting of chickens, turkeys, ducks, geese, quail, ostrich, emus and exotic birds such as parrots, cockatoos and cockatiels. More preferably, the avian subject to be tested is a chicken, turkey, goose or quail.

"Pathogenic strain of influenza A" when used in the context of distinguishing between different strains of influenza virus means a "notifiable avian influenza" (NAI) virus according to the guidelines set forth by the OIE World Organization for Animal Health, World Health Organization or their designated representatives e.g., as set forth in the OIE "Manual of Diagnostic Tests and Vaccines for Terrestrial Animals, 5th edition, 2004 (www.oie.int). Further, the subject pathogenic strain has "high pathogenicity" in a representative test for virulence or an H5 or H7 virus with an influenza A hemmagglutinin (HA) precursor protein HA0 cleavage site amino acid sequence that is similar to any of those that have been observed in virulent viruses, i.e., as defined by the OIE or a representative similar national or international organization or trade association. Representative examples of HA0 cleavage site amino acid sequences in virulent H5 and H7 strains of influenza A comprise multiple basic amino acids (arginine or lysine) at the cleavage site of the viral precursor hemagglutinin protein, e.g., where low virulence strains of H7 viruses have PEIPKGR*GLF (SEQ ID NO:5) or PENPKGR*GLF (SEQ ID NO:6) highly pathogenic strains have-PEIPKKKKR*GLF (SEQ ID NO:7), PETPKRKRKR*GLSF SEQ ID NO:8), PEIPKKREKR*GLF (SEQ ID NO:9) or PETPKRRRR*GLF (SEQ ID NO:10). Current representative tests for virulence include inoculation of 4-8 week old chickens with infectious virus wherein strains are considered to be highly pathogenic if they cause more than 75% mortality within 10 days; and/or, any virus that has an intravenous pathogenicity index (IVPI) greater than 1.2, wherein intravenously inoculated birds are examined at 24-hour intervals over a 10-day period; scored for "0", normal; "1" sick; "2" severely sick"; "3" dead; and, the mean score calculated as the IVPI. The latter highly pathogenic strains are referred to by the OIE as a "highly pathogenic NAI Virus" (HPNIA). Current representative examples of NAI include the H5 and H7 strains of influenza A. Current representative examples of HPNIA include H5N1.

"Less Pathogenic strain of influenza A" means an avian influenza A that is notifiable, i.e., an NAI isolate (supra), but which is not pathogenic for chickens and does not have an HA0 cleavage site amino acid sequence similar to any of those that have been observed in virulent viruses, i.e., a strain referred to by the OIE as a "low pathogenicity avian influenza (LPAI). Can we have an example of a less pathogenic strain.

Strains of influenza A that are not classified as highly pathogenic or less pathogenic are referred to as seasonal flu. Most strains of influenza A H1N1 are seasonal flu. However, one strain responsible for the 1918 Spanish flu is highly pathogenic.

"PDZ domain" means an amino acid sequence homologous over about 90 contiguous amino acids; preferably about 80-90; more preferably, about 70-80, more preferably about 50-70 amino acids with the brain synaptic protein PSD95, the Drosophila septate junction protein Discs-Large (DLG) and/or the epithelial tight junction protein ZO1 (ZO1). Representative examples of PDZ domains are also known in the art as Discs-Large homology repeats ("DHRs") and "GLGF" repeats (SEQ ID NO:26). Examples of PDZ domains are found in diverse membrane-associated proteins including members of the MAGUK family of guanylate kinase homologs, several protein phosphatases and kinases, neuronal nitric oxide synthase, tumor suppressor proteins, and several dystrophin-associated proteins, collectively known as syntrophins. The instant PDZ domains encompass both natural and non-natural amino acid sequences. Representative examples of PDZ domains include polymorphic variants of PDZ proteins, as well as, chimeric PDZ domains containing portions of two different PDZ proteins and the like. Preferably, the instant PDZ domains contain amino acid sequences which are substantially identical to those disclosed in U.S. patent application Ser. No. 10/485,788 (filed Feb. 3, 2004), International patent application PCT/US03/285/28508 (filed Sep. 9, 2003), International patent application PCT/US01/44138 (filed Nov. 9, 2001), incorporated herein by reference in their entirety. Representative non-natural PDZ domains include those in which the corresponding genetic code for the amino acid sequence has been mutated, e.g., to produce amino acid changes that alter (strengthen or weaken) either binding or specificity of binding to PL. Optionally a PDZ domain or a variant thereof has at least 50, 60, 70, 80 or 90% sequence identity with a PDZ domain from at least one of brain synaptic protein PSD95, the Drosophila septate junction protein Discs-Large (DLG) and/or the epithelial tight junction protein ZO1 (ZO1), and animal homologs. Optionally a variant of a natural PDZ domain has at least 90% sequence identity with the natural PDZ domain. Sequence identities of PDZ domains are determined over at least 70 amino acids within the PDZ domain, preferably 80 amino acids, and more preferably 80-90 or 80-100 amino acids. Amino acids of analogs are assigned the same numbers as corresponding amino acids in the natural human sequence when the analog and human sequence are maximally aligned. Analogs typically differ from naturally occurring peptides at one, two or a few positions, often by virtue of conservative substitutions. The term "allelic variant" is used to refer to variations between genes of different individuals in the same species and corresponding variations in proteins encoded by the genes. An exemplary PDZ domain for PSD95 d2 is provided as SEQ ID NO: 1.

"PDZ protein", used interchangeably with "PDZ-domain containing polypeptides" and "PDZ polypeptides", means a naturally occurring or non-naturally occurring protein having a PDZ domain (supra). Representative examples of PDZ proteins have been disclosed previously (supra) and include CASK, MPP1, DLG1, DLG2, PSD95, NeDLG, TIP-33, TIP-43, LDP, LIM, LIMK1, LIMK2, MPP2, AF6, GORASP1, INADL, KIAA0316, KIAA1284, MAGI1, MAST2, MINT1, NSP, NOS1, PAR3, PAR3L, PAR6 beta, PICK1, Shank 1, Shank 2, Shank 3, SITAC-18, TIP1, and ZO-1. The instant non-natural PDZ domain polypeptides useful in screening assays may contain e.g. a PDZ domain that is smaller than a natural PDZ domain. For example a non-natural PDZ domain may optionally contain a "GLGF" motif, i.e., a motif having the GLGF amino acid sequence (SEQ ID NO:26), which typically resides proximal, e.g. usually within about 10-20 amino acids N-terminal, to an PDZ domain. The latter GLGF motif (SEQ ID NO:26), and the 3 amino acids immediately N-terminal to the GLGF motif (SEQ ID NO:26) are often required for PDZ binding activity. Similarly, non-natural PDZ domains may be constructed that lack the β-sheet at the C-terminus of a PDZ domain, i.e., this region may often be deleted from the natural PDZ domain without affecting the binding of a PL. Some exemplary PDZ proteins are provided and the GI or accession numbers are provided in parenthesis: PSMD9 (9184389), af6 (430993), AIPC (12751451), ALP (2773059), APXL-1 (13651263), MAGI2 (2947231), CARDI1 (1282772), CARDI4 (13129123), CASK (3087815), CNK1 (3930780), CBP (3192908), Densin 180 (16755892), DLG1 (475816), DLG2 (12736552), DLG5 (3650451), DLG6 splice var 1 (14647140), DLG6 splice var 2 (AB053303), DVL1 (2291005), DVL2 (2291007), DVL3 (6806886), ELFIN 1 (2957144), ENIGMA (561636), ERBIN (8923908), EZRIN binding protein 50 (3220018), FLJ00011 (10440342), FLJ11215 (11436365), FLJ12428 (BC012040), FLJ12615 (10434209), FLJ20075 Semcap2 (7019938), FLJ21687 (10437836), FLJ31349 (AK055911), FLJ32798 (AK057360), GoRASP1 (NM031899), GoRASP2 (13994253), GRIP1 (4539083), GTPase Activating Enzyme (2389008), Guanine Exchange Factor (6650765), HEMBA 1000505 (10436367), HEMBA 1003117 (7022001), HSPC227 (7106843), HTRA3 (AY040094), HTRA4 (AL576444), INADL (2370148), KIAA0147 Vartul (1469875), KIAA0303 MAST4 (2224546), KIAA0313 (7657260), KIAA0316 (6683123), KIAA0340 (2224620), KIAA0380 (2224700), KIAA0382 (7662087), KIAA0440 (2662160), KIAA0545 (14762850), KIAA0559 (3043641), KIAA0561 MAST3 (3043645), KIAA0613 (3327039), KIAA0751 RIM2 (12734165), KIAA0807 MAST2 (3882334), KIAA0858 (4240204), KIAA0902 (4240292), KIAA0967 (4589577), KIAA0973 SEMCAP3 (5889526), KIAA1202 (6330421), KIAA1222 (6330610), KIAA1284 (6331369), KIAA1389 (7243158), KIAA1415 (7243210), KIAA1526 (5817166), KIAA1620 (10047316), KIAA1634 MAGI3 (10047344), KIAA1719 (1267982), LIM Mystique (12734250), LIM (3108092), LIMK1 (4587498), LIMK2 (1805593), LIM-RIL (1085021), LU-1 (U52111), MAGI1 (3370997), MGC5395 (BC012477), MINT1 (2625024), MINT3 (3169808) MPP1 (189785), MPP2 (939884), MPP3 (1022812), MUPP1 (2104784), NeDLG (10853920), Neurabin II (AJ401189), NOS1 (642525), novel PDZ gene (7228177), Novel Serine Protease (1621243), Numb Binding Protein (AK056823), Outer Membrane Protein (7023825), p55T (12733367), PAR3 (8037914), PAR3-like (AF428250), PAR6 (2613011), PAR6BETA (13537116), PAR6GAMMA (13537118), PDZ-73 (5031978), PDZK1 (2944188), PICK1 (4678411), PIST (98394330), prIL16 (1478492), PSAP (6409315), PSD95 (3318652), PTN-3 (179912), PTN-4 (190747), PTPL1 (515030), RGS12 (3290015), RGS3 (18644735), Rho-GAP10 (NM020824), Rhophilin-like (14279408), Serine Protease (2738914), Shank 2 (6049185), Shank 3 (AC000036), Shroom (18652858), Similar to GRASP65 (14286261), Similar to Ligand of Numb px2 (BC036755), Similar to PTP Homolog (21595065), SIP1 (2047327), SITAC-18 (8886071), SNPCIIA (20809633), Shank 1 (7025450), Syntenin (2795862), Syntrophin 1 alpha (1145727), Syntrophin beta 2 (476700), Syntrophin gamma 1 (9507162), Syntrophin gamma 2 (9507164), TAX2-like protein (3253116), TIAM 1 (4507500), TIAM 2 (6912703), TIP 1 (2613001), TIP2 (2613003), TIP33 (2613007), TIP43 (2613011), X-11 beta (3005559), ZO-1 (292937), ZO-2 (12734763), ZO-3 (10092690).

"PDZ ligand", abbreviated "PL", means a naturally occurring protein that has an amino acid sequence which binds to and forms a molecular interaction complex with a PDZ-domain. Representative examples of PL have been provided previously in prior US and International patent applications (supra). Additional examples of influenza A PL are provided in the Examples section, below.

"Specific binding" between a binding agent, e.g., an antibody or a PDZ domain and an NS1 protein refers to the ability of a capture- or detection-agent to preferentially bind to a particular viral analyte that is present in a mixture of different viral analytes. For example, some antibodies described in the application specifically bind to NS1 from influenza B without specifically binding to NS1 from influenza A, and vice versa. Specific binding also means a dissociation constant (KD) that is less than about $10^{-6}$ M; preferably, less than about 10-7M; and, most preferably, less than about $10^{-8}$ M, In some methods, specific binding interaction is capable of discriminating between proteins having or lacking a PL with a discriminatory capacity greater than about 10- to about 100-fold; and, preferably greater than about 1000- to about 10,000-fold.

"Capture agent/analyte complex" is a complex that results from the specific binding of a capture agent, with an analyte, e.g. an influenza viral NS1 protein. A capture agent and an analyte specifically bind, i.e., the one to the other, under conditions suitable for specific binding, wherein such physicochemical conditions are conveniently expressed e.g. in terms of salt concentration, pH, detergent concentration, protein concentration, temperature and time. The subject conditions are suitable to allow binding to occur e.g. in a solution; or alternatively, where one of the binding members is immobilized on a solid phase. Representative conditions so-suitable are described in e.g., Harlow and Lane, "Antibodies: A Laboratory Manual", Cold Spring Harbor Laboratory, Cold Spring Harbor, N.Y. (1989). Suitable conditions preferably result in binding interactions having dissociation constants (KD) that are less than about $10^{-6}$ M; preferably, less than about $10^{-7}$ M; and, most preferably less than about $10^{-8}$ M.

"Solid phase" means a surface to which one or more reactants may be attached electrostatically, hydrophobically, or covalently. Representative solid phases include e.g.: nylon 6; nylon 66; polystyrene; latex beads; magnetic beads; glass beads; polyethylene; polypropylene; polybutylene; butadiene-styrene copolymers; silastic rubber; polyesters; polyamides; cellulose and derivatives; acrylates; methacrylates; polyvinyl; vinyl chloride; polyvinyl chloride; polyvinyl fluoride; copolymers of polystyrene; silica gel; silica wafers glass; agarose; dextrans; liposomes; insoluble protein metals; and, nitrocellulose. Representative solid phases include those formed as beads, tubes, strips, disks, filter papers, plates and the like. Filters may serve to capture analyte e.g. as a filtrate, or act by entrapment, or act by covalently binding. A solid phase capture reagent for distribution to a user may consist of a solid phase coated with a "capture reagent", and packaged (e.g., under a nitrogen atmosphere) to preserve and/or maximize binding of the capture reagent to an influenza NS1 analyte in a biological sample.

Biological samples include tissue fluids, tissue sections, biological materials carried in the air or in water and collected there from e.g. by filtration, centrifugation and the like, e.g., for assessing bioterror threats and the like. Alternative biological samples can be taken from fetus or egg, egg yolk, and amniotic fluids. Representative biological fluids include urine, blood, plasma, serum, cerebrospinal fluid, semen, lung lavage fluid, feces, sputum, mucus, water carrying biological materials and the like. Alternatively, biological samples include nasopharyngeal or oropharyngeal swabs, nasal lavage fluid, tissue from trachea, lungs, air sacs, intestine, spleen, kidney, brain, liver and heart, sputum, mucus, water carrying biological materials, cloacal swabs, sputum, nasal and oral mucus, and the like. Representative biological samples also include foodstuffs, e.g., samples of meats, processed foods, poultry, swine and the like. Biological samples also include contaminated solutions (e.g., food processing solutions and the like), swab samples from out-patient sites, hospitals, clinics, food preparation facilities (e.g., restaurants, slaughter houses, cold storage facilities, supermarket packaging and the like). Biological samples may also include in situ tissues and bodily fluids (i.e., samples not collected for testing), e.g., the instant methods may be useful in detecting the presence or severity or viral infection in the eye e.g., using eye drops, test strips applied directly to the conjunctiva; or, the presence or extent of lung infection by e.g. placing an indicator capsule in the mouth or nasopharynx of the test subject. Alternatively, a swab or test strip can be placed in the mouth. The biological sample may be derived from any tissue, organ or group of cells of the subject. In some embodiments a scrape, biopsy, or lavage is obtained from a subject. Biological samples may include bodily fluids such as blood, urine, sputum, and oral fluid; and samples such as nasal washes, swabs or aspirates, tracheal aspirates, chancre swabs, and stool samples. Methods are known to those of skill in the art for the collection of biological specimens suitable for the detection of individual pathogens of interest, for example, nasopharyngeal specimens such as nasal swabs, washes or aspirates, or tracheal aspirates in the case of high risk influenza A viruses involved in respiratory disease, oral swabs and the like. Optionally, the biological sample may be suspended in an isotonic solution containing antibiotics such as penicillin, streptomycin, gentamycin, and mycostatin.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample that is not found naturally.

"Subject", is used herein to refer to a man and domesticated animals, e.g. mammals, fishes, birds, reptiles, amphibians and the like.

"Signal generating compound", abbreviated "SGC", means a molecule that can be linked to a PL or a PDZ (e.g. using a chemical linking method as disclosed further below and is capable of reacting to form a chemical or physical entity (i.e., a reaction product) detectable in an assay according to the instant disclosure. Representative examples of reaction products include precipitates, fluorescent signals, compounds having a color, and the like. Representative SGC include e.g., bioluminescent compounds (e.g., luciferase), fluorophores (e.g., below), bioluminescent and chemiluminescent compounds, radioisotopes (e.g., $^{131}I$, $^{125}I$, $^{14}C$, $^{3}H$, $^{35}S$, $^{32}P$ and the like), enzymes (e.g., below), binding proteins (e.g., biotin, avidin, streptavidin and the like), magnetic particles, chemically reactive compounds (e.g., colored stains), labeled oligonucleotides; molecular probes (e.g., CY3, Research Organics, Inc.), and the like. Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Representative SGC's useful in a signal generating conjugate include the enzymes in: IUB Class 1, especially 1.1.1 and 1.6 (e.g., alcohol dehydrogenase, glycerol dehydrogenase, lactate dehydrogenase, malate dehydrogenase, glucose-6-phosphate dehydrogenase, glyceraldehyde-3-phosphate dehydrogenase and the like); IUB Class 1.11.1 (e.g., catalase, peroxidase, amino acid oxidase, galactose oxidase, glucose oxidase, ascorbate oxidase, diaphorase, urease and the like); IUB Class 2, especially 2.7 and 2.7.1 (e.g., hexokinase and the like); IUB Class 3, especially 3.2.1 and 3.1.3 (e.g., alpha amylase, cellulase, β-galacturonidase, amyloglucosidase, β-glucuronidase, alkaline phosphatase, acid phosphatase and the like); IUB Class 4 (e.g., lyases); IUB Class 5 especially 5.3 and 5.4 (e.g., phosphoglucose isomerase, trios phosphatase isomerase, phosphoglucose mutase and the like.) Signal generating compounds also include SGC whose products are detectable by fluorescent and chemiluminescent wavelengths, e.g., luciferase, fluorescence emitting metals such as $^{152}Eu$, or others of the lanthanide series; compounds such as luminol, isoluminol, acridinium salts, and the like; bioluminescent compounds such as luciferin; fluorescent proteins; and the like. Fluorescent proteins include, but are not limited to the following: namely, (i) green fluorescent protein (GFP), i.e., including, but not limited to, a "humanized" versions of GFP wherein codons of the naturally-occurring nucleotide sequence are exchanged to more closely match human codon bias; (ii) GFP derived from *Aequoria victoria* and derivatives thereof, e.g., a "humanized" derivative such as Enhanced GFP, which are available commercially, e.g., from Clontech, Inc.; (iii) GFP from other species such as *Renilla reniformis, Renilla mulleri*, or *Ptilosarcus guemyi*, as described in, e.g., WO 99/49019 and Peelle et al. (2001) J. Protein Chem. 20:507-519; (iv) "humanized" recombinant GFP (hrGFP) (Stratagene); and, (v) other fluorescent and colored proteins from *Anthozoan* species, such as those described in Matz et al. (1999) Nature Biotechnol. 17:969-973; and the like. The subject signal generating compounds may be coupled to a PL or PDZ domain polypeptide. Attaching certain SGC to proteins can be accomplished through metal chelating groups such as EDTA. The subject SGC share the common property of allowing detection and/or quantification of an influenza PL analyte in a test sample. The subject SGC are detectable using a visual method; preferably, an a method amenable to automation such as a spectrophotometric method, a fluorescence method, a chemiluminescent method, a electrical nanometric method involving e.g., a change in conductance, impedance, resistance and the like and a magnetic field method.

The epitope of a mAb is the region of its antigen to which the mAb binds. Two antibodies bind to the same or overlapping epitope if one competitively inhibits (blocks) binding of a prototypical antibody defining the competition group to the antigen (an NS1 protein of influenza A or influenza B, in the assays below). That is, a 3-fold of 5-fold excess of one antibody inhibits binding of the other by at least 50% but preferably 75%, 90% or even 99% as measured in a competitive binding assay compared to a control lacking the competing antibody (see, e.g., Junghans et al., Cancer Res. 50:1495, 1990, which is incorporated herein by reference). Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Detecting "presence" or "absence" of an analyte includes qualitative assays in which only presence or absence of analyte is detected and quantitative assays in which presence of analyte is detected as well as an amount of analyte present.

DETAILED DESCRIPTION OF THE INVENTION

I. General

Commonly owned applications PCT/US06/41748 and U.S. Ser. No. 11/481,411 set out the general concept that NS1 protein of influenza protein is an abundant protein in subjects infected with influenza A and B and thus useful for detection of these viruses. The '411 application also shows that the NS1 proteins of influenza A (although not influenza B) contain PL regions. These PL regions can be readily detected using PDZ domains and thus provide a basis for detecting influenza A and distinguishing it from other types of influenza. Moreover, PL's from pathogenic subtypes of influenza A differ from those in seasonal subtypes of influenza. Differential detection of PL's using different PDZ domains thus provides a basis to distinguish between pathogenic and seasonal subtypes of influenza A.

The present application reiterates some of the concepts mentioned above and describes preferred formats for detecting influenza A and its subtypes and/or influenza B. Many of these preferred formats employ pan-specific antibodies (i.e., that react with all or at least multiple strains within an influenza type).

II. Influenza Viruses and their NS1 Proteins

The influenza viruses belong to the Orthomyxoviridae family, and are classified into types A, B, and C based upon antigenic differences in their nucleoprotein (NP) and matrix protein (M1). Further subtyping into strains is commonly based upon assessing the type of antigen present in two virion glycoproteins, namely, hemagglutinin (HA; H) and neuraminidase (NA; N). HA and NP are virulence factors mediating attachment of the virion to the surface of host cells. Thus, H5N1, H1N1 and H3N2 are examples of subtypes of influenza A. Within each subtype there are hundreds of strains. M1 protein is thought to function in virus assembly and budding, whereas NP functions in RNA replication and transcription. In addition to these virion proteins, two other non-structural, i.e., non-virion, proteins are expressed in virus infected cells which are referred to as non-structural proteins 1 and 2 (NS1; NS2). The non-structural viral protein NS1 has multiple functions including the regulation of splicing and nuclear export of cellular mRNAs and stimulation of translation, as well as the counteracting of host interferon ability.

The NS1 protein has been identified and sequenced in influenza viruses and exemplary sequences can be found in the NCBI database. The NS1 proteins from influenza A, B and C do not in general show antigenic cross reactivity. Within a type (e.g., influenza A), there is considerable variation in sequence between subtypes, but some antigenic crossreactivity depending on which antibody is used. The GenBank accession numbers of some exemplary NS1 sequences from influenza type A, subtypes H1N1, H3N2 and H5N1 respectively, are CY003340, CY003324, DQ266101. The GenBank accession numbers of some exemplary NS1 sequences from influenza type B are AAA43690 and BAD29872. The NS1 protein in other strains of influenza either influenza type A, type B or type C, means a protein having the greatest sequence similarity to one of the proteins identified as an NS1 protein in known influenza strains of the same subtype, using as sequence for example, one of the GenBank accession numbers given above.

II. PDZ domains for Detection of Influenza A

Table 1 below lists the PL regions of influenza A subtypes H5N1, H1N1 and H3N2. H5N1 is the most clinically relevant subtype of pathogenic strains. H1N1 and H3N2 are the most clinically relevant subtypes of seasonal influenza A. The table also indicates whether various PDZ domains bind to the indicated PL. The table can be used to select PDZ domains for differential detection of pathogenic and seasonal subtypes of influenza A. For example, a PSD95 domain is useful for detecting pathogenic subtypes of influenza A, and INADL domain 8 is useful for detecting seasonal subtypes of influenza A. The PSD95 domain can be any of PDZ domains 1, 2, and 3 of PSD95, or combinations thereof. A preferred detection reagent is a protein formed from three copies of domain 2 of PSD95 in a PSD95. That is, three tandem copies interspersed by segments of PSD95 flanking its PDZ domains. In such a protein two of the copies of domain 2 of PSD95 effectively replace natural domains 1 and 3 of PSD95. Another preferred detection reagent is a protein containing PDZ domains 1, 2 and 3 of PSD95.

TABLE 1

| Influenza A subtypes | PL | PSD-95 D2 | PSD95 D1, D2, D3 | INADL d8 |
|---|---|---|---|---|
| H5N1 | ESEV | ++ | ++ | – |
| H1N1 | RSEV | + | +– | ++ |
| H3N2 | RSKV | – | – | ++ |

Assay conditions such as buffer and temperature can be used to modulate binding to favor detection of a particular strain or differentiation among the different strains. The symbols used in the table mean as follows: ++relatively strong binding, +detectable but relatively weak binding, +/–detectable but relatively weak binding or undetectable binding, –undetectable binding. Detectable binding means that the signal from binding is greater in a sample containing NS1 of the indicated subtype relative to a control lacking the NS1 of the indicated subtype to a significant extent taking into account random variation due to experimental error. Undetectable binding means that the signal from binding to a sample containing NS1 of the indicated subtype is within the margin of error from the signal in a control lacking NS1 of the indicated subtype.

A preferred format for subtyping influenza A uses a PDZ from PDS95 as shown in the table in combination with an INDAL PDZ domain 8. As a general rule, detectable binding of the PSD95 domain without binding of the INDAL domain or significantly stronger (i.e., stronger beyond experimental error) binding of the PSD95 domain that that of the INADL domain is an indication that the influenza A subtype is H5N1 (pathogenic). Conversely, detectable binding of the INADL domain to the sample without detectable binding of the PSD95 domain to the sample or significantly stronger binding of the INADL domain to the sample than of the PSD95 to the sample is an indication that the sample contains an influenza A subtype H1N1 or H3N2 (both seasonal influenza). Detectable but weak binding of PSD95 domain 2 to the sample compared with undetectable binding distinguishes H1N1 from H3N2 as indicated in the table. Detectable but relatively weak binding of PSD95 domains 1, 2 and 3 to a sample compared with binding of INADL to the sample is also an indication that the subtype is H1N1.

III. Antibodies for Detection of Influenza A and Influenza B

The invention provides a collection of pan-specific antibodies for detection of influenza A. A pan specific antibody for influenza A specifically binds to the NS1 protein from at least 2, 3 or 5 or all or substantially all known strains of influenza A. Likewise a pan specific antibody for influenza B specifically binds to the NS1 protein from at least 2, 3, 5 or all or substantially all known strains of influenza B.

Pan-specific antibodies can be defined by reference to either a numerically defined epitope or by a competition group defined by reference to an exemplary antibody. For influenza A, pan specific antibodies preferably specifically bind to an epitope within residues 8-21, 9-20, 29-38 or 45-49 of FIG. 1A or FIG. 2. The X's in this sequence can be any amino acid but are preferably an amino acid occupying the corresponding position in an NS1 protein from a strain of influenza, and more preferably the consensus amino acid occupying the corresponding position from at least two or preferably all known strains of influenza A. A consensus sequence of influenza A is provided in FIG. 2. Some pan specific antibodies specifically bind to an epitope within residues 9-11 or 13-16 of FIG. 1A.

Pan specific antibodies can also be defined by a competition group; the antibodies within a competition group compete with one another for specific binding to the same antigen (i.e., an SN1 protein of influenza A or influenza B). Table 2 shows competition groups of panspecific antibodies binding to an NS1 protein of influenza A.

TABLE 2

| Anti-Influenza A NS1 competition group | mAb Ref. | | |
|---|---|---|---|
| Group A | F64 3H3 | F68 4H9 | Comment: Partial competition |
| Group B | F68 8E6 | F80 3D5 | Comment: Slight/ partial competition |

Each group is defined by a prototypical antibody (in column 2) with which other antibodies (column 3) in the group compete. Groups A, B and C are preferred. All of these antibodies bind to the NS1 protein from at least strains H5N1, H1N1 and H3N2. The antibodies in different groups do not compete with each other.

Table 3 shows preferred antibodies for use in sandwich detection of the H5N1 pathogenic strain of influenza. In such assays, a preferred capture agent is PSD95 domains 1, 2 and 3, and a preferred detection agent is an antibody preferably from Group A, or alternatively Group C or D.

TABLE 3

| Anti-Influenza A H5N1 NS1 competition group | Mab or PDZ Ref. | |
|---|---|---|
| Group A | F68 4B2 | F68 8E6 |
| Group B | PSD95(1, 2, 3) | |
| Group C | F64 3H3 | |

Table 4 shows competition groups for panspecific antibodies binding to the NS1 protein of influenza B.

TABLE 4

| Anti-Influenza B NS1 competiton group | mAb Ref. | | | | |
|---|---|---|---|---|---|
| Group A: F89-1F4 competitors | F89 1F4 | F89 6D11 | F89 6G1 | F89 6H3 | F89 6B5 |
| Group B: F94-3A1 competitors | F94 3A1 | F94 7G2 | | | |
| Group C | F94-1F8, F94-1F9 and F94-5E5 compete w/each other | | | | |

Table 5 shows pairs of competing capture and detection antibodies. Detection antibodies are shown in the first row of the table and capture antibodies in the first column. Competition is shown with a C.

TABLE 5

| | F89-1F4 | F89-1G8 | F89-4D7 | F89-6B5 | F89-6D11 | F89-6G1 | F89-6H3 | F94-1F8 | F94-1F9 | F94-3A1 | F94-5E5 | F94-7A1 | F94-7G2 |
|---|---|---|---|---|---|---|---|---|---|---|---|---|---|
| F89-1F4 | C | | | C | C | C | C | | | | | | |
| F89-1G8 | | C | | | | | | | | | | | |
| F89-4D7 | | | C | | | | | | | | | | |
| F89-6B5 | C | | | C | | | | | | | | | |
| F89-6D11 | C | | | | C | | | | | | | | |
| F89-6G1 | C | | | | | C | | | | | | | |
| F89-6H3 | C | | | | | | C | | | | | | |
| F94-1F8 | | | | | | | | C | C | | C | | |
| F94-1F9 | | | | | | | | C | C | | C | | |
| F94-3A1 | | | | | | | | | | C | | | C |
| F94-5E5 | | | | | | | | C | C | | C | | |
| F94-7A1 | | | | | | | | | | | | C | |
| F94-7G2 | | | | | | | | | | C | | | C |

Pan-specific antibodies for influenza type B can also be described by epitope specificity with reference to the consensus sequence of NS1 proteins from influenza B strains shown in FIG. 2. Preferred antibodies specifically bind to an epitope occurring within residues 10-28, 40-45, 50-57, 67-74, 84-100, 154-159, 169-173, 185-191, 212-224, 226-240 of FIG. 2, and particularly underlined regions thereof, which indicate residues that are invariable between different strains of influenza type B. Residues included in one of the above regions that are not underlined (i.e., vary between influenza type B strains) can be occupied by the consensus residue occupying that position shown in FIG. 2 or the residue occupying that position in any strain of influenza type B.

Figure 13:
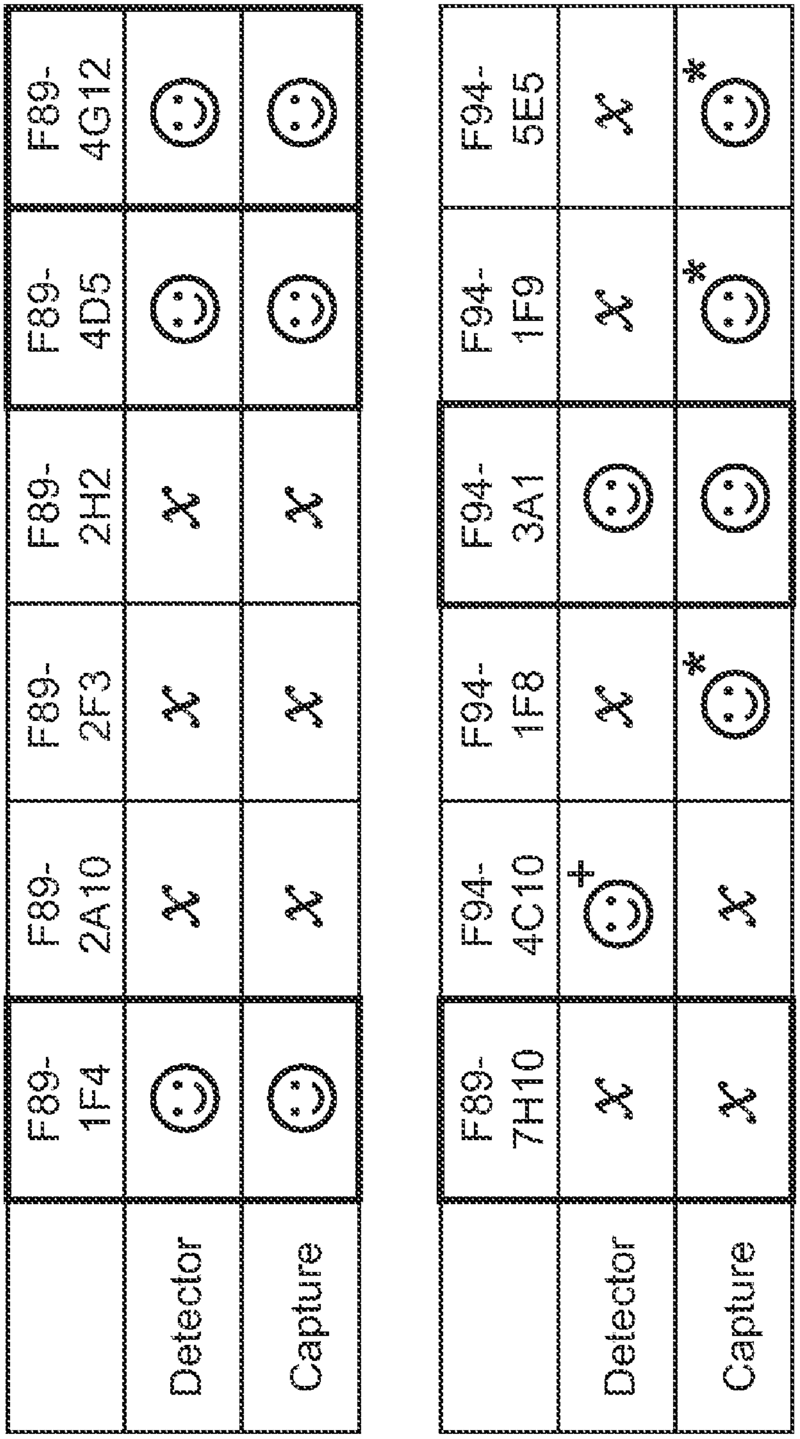
FIG. 13: Chart showing suitable combinations of capture and detection antibody for detection of NS1 from influenza B.

Preferred combinations of antibodies to NS1 of influenza B for use in sandwich assays are indicated with a happy face in FIG. 13.

The antibodies used can be nonhuman, humanized, chimeric, veneered, or human. Use of such antibodies is advantageous in avoiding false positives or negatives due to the presence of HAMA or heterophilic antibodies in the sample (U.S. Pat. No. 6,680,209). Humanized, chimeric or veneered versions of the antibodies listed in the tables above are preferred. Such antibodies can also be used as pharmaceutical agents in treatment of influenza A or B. Antibodies can be made from antigen-containing fragments of the protein by standard procedures according to the type of antibody (see, e.g., Kohler, et al., Nature, 256:495, (1975); and Harlow & Lane, Antibodies, A Laboratory Manual (C.S.H.P., NY, 1988) Queen et al., Proc. Natl. Acad. Sci. USA 86:10029-10033 (1989) and WO 90/07861; Dower et al., WO 91/17271 and McCafferty et al., WO 92/01047 (each of which is incorporated by reference for all purposes).

Immunization can be biased to generate panspecific antibodies by immunizing with multiple strains of influenza A or B, or by immunizing with one strain and boosting with another. Alternatively, one can use a fragment from a highly conserved region of influenza A (e.g., 8-21, 9-20, 29-38 or 45-49 or at least three contiguous amino acids of any of these of SEQ ID NO:1) or B NS1 (e.g., 10-28, 40-45, 50-57, 67-74, 84-100, 154-159, 169-173, 185-191, 212-224, or 226-240 of SEQ ID NO:4 or subfragments of at least three contiguous amino acids thereof) as the immunogen. Conversely, to generate a monospecific antibody, immunization with NS1 of a single strain, or a fragment of NS1 from a nonconserved region (e.g., a PL region of influenza A) is preferred.

The term "antibody" or "immunoglobulin" is used to include intact antibodies and binding fragments thereof. which they were derived for specific binding to an antigen Typically, fragments compete with the intact antibody from fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody.

Unless otherwise indicated the antibodies described in the present application are mouse antibodies produced from hybridomas.

IV. Other Binding Agents

Although pan-specific antibodies are preferred for use in detecting the NS1 protein, any binding agent with specific affinity for NS1 of influenza can be used as an antibody surrogate. Surrogates includes peptides from randomized phage display libraries screened against NS1 from influenza A or B. Surrogates also include aptamers. Aptamers are RNA or DNA molecules selected in vitro from vast populations of random sequence that recognize specific ligands by forming binding pockets. Allosteric ribozymes are RNA enzymes whose activity is modulated by the binding of an effector molecule to an aptamer domain, which is located apart from the active site. These RNAs act as precision molecular switches that are controlled by the presence or absence of a specific effector. Aptamers can bind to nucleic acids, proteins, and even entire organisms. Aptamers are different from antibodies, yet they mimic properties of antibodies in a variety of diagnostic formats. Thus, aptamers can be used as a surrogate for panspecific antibodies.

Likewise, although PDZ domains are preferred for detecting PL regions of NS1, an antibody specifically binding to a PL region of a particular NS1 protein of influenza A can be used as a surrogate for a PDZ domain specifically binding to that region.

V. Detection Methods

1. Detection of Influenza A Subtypes

The invention provides methods of distinguishing between pathogenic and seasonal subtypes of influenza A as discussed above. A preferred format uses one or more PDZ domain as the capture reagent and one or more pan-specific antibodies as the detection reagent. As discussed above, use of domain 2 or domains 1, 2 and 3 of PSD95 and/or domain 8 of INADL are preferred as PDZ domain detection reagents. Preferred panspecific antibodies for use with a PDZ capture reagent are a pan specific antibody F68 8E6 (or an antibody that competes therewith) or F68 4B2 (or an antibody that competes therewith) as the detection antibody. The same or different panspecific antibody can be used with different PDZ domains in the same assay.

2. Detection of Influenza A with Pan Specific Antibodies

The invention also provides methods of detecting influenza A in a manner that does not necessarily distinguish between subtypes of influenza A but can distinguish between influenza A and influenza B (or C). Such methods are performed using at least two pan specific antibodies to the NS1 protein of influenza A binding to different epitopes. The two panspecific antibodies specifically bind to different epitopes defined numerically as described above or can be selected from different competition groups. Detection is preferably performed using a sandwich or lateral flow format as described in more detail below. One preferred combination of antibodies for detecting influenza A is F64 3H3 (or antibody that competes therewith) as the capture antibody, and F80 3D5 (or an antibody that competes therewith) as the detection antibody. Another preferred combination is F68 4H9 (or an antibody that competes therewith) as the capture antibody and F68 8E6 (or an antibody that competes therewith) as the detection antibody.

Detecting of influenza A using two panspecific antibodies can be combined with differential detection of influenza A subtypes as described in (1) above. Such an assay indicates both whether influenza A is present, and if so, whether a pathogenic or seasonal subtype is present. The non-subtype-specific and subtype-specific assays can be performed separately or combined. One suitable format for combining the assays is to attach PDZ domain(s) for use in differential analysis to different regions of the same solid phase as an antibody capture reagent for use in non-subtype specific analysis. Binding of a PDZ domain to an NS1 protein in the sample can be detected using a panspecific detection antibody. The panspecific detection antibody used to detect binding of the PDZ domain to the NS1 protein can be the same or different as the panspecific antibody used for non-subtype specific analysis. Thus, in a preferred format, a PSD95 domain, an INADL domain 8 and a panspecific capture antibody for influenza A are attached to different regions of a support, and a common panspecific detection antibody (binding to a different epitope than the panspecific capture antibody) is used to detect binding of each of the capture reagents to an influenza A NS1 protein if present in the sample, as discussed above.

3. Detection of Influenza B with Pan Specific Antibodies

Influenza B can be detected using first and second panspecific antibodies to the NS1 protein of influenza B in analogous fashion to the assays described for detecting the NS1 protein of influenza A, as described above. Such methods are performed using at least two pan specific antibodies to the NS1 protein of influenza B binding to different epitopes. The two panspecific antibodies bind different epitopes defined numerically as described above or can be selected from different competition groups. Detection is preferably performed using a sandwich or lateral flow format as described in more detail below. A preferred combination of antibodies for detection of influenza B uses F89 6B5 (or an antibody that competes therewith) as the capture antibody and F94 3A1 (or an antibody that competes therewith) or F94 1F9 (or an antibody that competes therewith) as the detection or detection antibody. Competition of antibodies is determined by binding to an NS1 protein of influenza B.

4. Combined Detection Influenza A and Influenza B

Each of the three assay types described above can effectively be combined to provide an assay capable of detecting influenza A (non-subtype specific), influenza B (non-subtype specific), influenza A (pathogenic subtype) and influenza A (seasonal subtype). The individual assays can be performed separately or together. One suitable format for combining the assays is to attach a panspecific capture antibody for the NS1 protein of influenza A, a panspecific capture antibody for the NS1 protein of influenza B, a PDZ domain for a PL of a pathogenic subtype of influenza A (e.g., a PSD95 domain as discussed above), and a PDZ domain for a PL of a seasonal subtype of influenza A (e.g., an INADL 8 domain) to a single support. The support is contacted with a sample from a subject and at least two panspecific detection antibodies. One detection antibody specifically binds to the NS1 protein of influenza A at an epitope different from the capture antibody to the NS1 protein of influenza A. The other detection antibody specifically binds to the NS1 protein of influenza B at an epitope different from the capture antibody to the NS1 protein of influenza B. The complexes that form indicate whether influenza A and/or B is present, and if influenza A is present whether the influenza A is pathogenic or seasonal.

VI. Detection Formats

The invention provides diagnostic capture and detect reagents useful in assay methods for identifying influenza A and/or B viruses in a variety of different types of biological samples. Such formats include immunoprecipitation, Western blotting, ELISA, radioimmunoassay, competitive and immunometric assays. See Harlow & Lane, *Antibodies, A Laboratory Manual* (CSHP NY, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Immunometric or sandwich assays are a preferred format (see U.S. Pat. Nos. 4,376,110, 4,486,530, 5,914,241, and 5,965,375). Such assays use one antibody or population of antibodies or a PDZ domain immobilized to a solid phase as a capture agent, and another antibody or population of antibodies or a PDZ domain in solution as detection agent. As discussed above, a combination of a capture PDZ domain and a detection antibody or vice versa is preferred for detection of influenza A. Typically, the detection agent is labeled. If an antibody population is used, the population typically contains antibodies binding to different epitope specificities within the target antigen. Accordingly, the same population can be used for both capture agent and detector agent. If monoclonal antibodies are used as detection and detection agents, first and second monoclonal antibodies having different binding specificities are used for the solid and solution phase. Capture and detection agents can be contacted with target antigen in either order or simultaneously. If the capture agent is contacted first, the assay is referred to as being a forward assay. Conversely, if the detection agent is contacted first, the assay is referred to as being a reverse assay. If target is contacted with both capture agent and detection agent simultaneously, the assay is referred to as a simultaneous assay. After contacting the sample with capture and detection antibodies, a sample is incubated for a period that usually varies from about 10 min to about 24 hr and is usually about 1 hr. A wash step can then be performed to remove components of the sample not specifically bound to the detection agent. When capture and detection agents are bound in separate steps, a wash can be performed after either or both binding steps. After washing, binding is quantified, typically by detecting label linked to the solid phase through binding of labeled solution antibody. Usually for a given pair of capture and detection agents and given reaction conditions, a calibration curve is prepared from samples containing known concentrations of target antigen. Concentrations of antigen in samples being tested are then read by interpolation from the calibration curve. Analyte can be measured either from the amount of labeled solution antibody bound at equilibrium or by kinetic measurements of bound labeled solution antibody at a series of time points before equilibrium is reached. The slope of such a curve is a measure of the concentration of target in a sample.

Competitive assays can also be used. In some methods, target antigen in a sample competes with exogenously supplied labeled target antigen for binding to an antibody or PDZ detection reagent. The amount of labeled target antigen bound to the detection reagent is inversely proportional to the amount of target antigen in the sample. The detection reagent can be immobilized to facilitate separation of the bound complex from the sample prior to detection (heterogeneous assays) or separation may be unnecessary as practiced in homogeneous assay formats. In other methods, the detection reagent is labeled. When the detection reagent is labeled, its binding sites compete for binding to the target antigen in the sample and an exogenously supplied form of the target antigen that can be, for example, the target antigen immobilized on a solid phase. Labeled detection reagent can also be used to detect antibodies in a sample that bind to the same target antigen as the labeled detection reagent in yet another competitive format. In each of the above formats, the detection reagent is present in limiting amounts roughly at the same concentration as the target that is being assayed.

Lateral flow devices are a preferred format. Similar to a home pregnancy test, lateral flow devices work by applying fluid to a test strip that has been treated with specific biologicals. Carried by the liquid sample, phosphors labeled with corresponding biologicals flow through the strip and can be captured as they pass into specific zones. The amount of phosphor signal found on the strip is proportional to the amount of the target analyte.

A sample suspected of containing influenza is added to a lateral flow device, the sample is allowed to move by diffusion and a line or colored zone indicates the presence of influenza. The lateral flow typically contains a solid support (for example nitrocellulose membrane) that contains three specific areas: a sample addition area, a capture area containing one or more antibodies to NS1, and a read-out area that contains one or more zones, each zone containing one or more labels. The lateral flow can also include positive and negative controls. Thus, for example a lateral flow device can be used as follows: an influenza A and/or B NS1 protein is separated from other viral and cellular proteins in a biological sample by bringing an aliquot of the biological sample into contact with one end of a test strip, and then allowing the proteins to migrate on the test strip, e.g., by capillary action such as lateral flow. One or more antibodies, and/or aptamers are included as capture and/or detect reagents. Methods and devices for lateral flow separation, detection, and quantification are described by, e.g., U.S. Pat. Nos. 5,569,608; 6,297,020; and 6,403,383 incorporated herein by reference in their entirety. As an example, a test strip can comprise a proximal region for loading the sample (the sample-loading region) and a distal test region containing an antibody to an NS1 protein and buffer reagents and additives suitable for establishing binding interactions between the antibody any influenza B NS1 protein in the migrating biological sample. In another example, the test strip comprises two test regions that contain different antibodies to NS1 from two different subtypes of influenza B i.e., each is capable of specifically interacting with a different influenza B analyte.

Suitable detectable labels for use in the above methods include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic (e.g., polystyrene, polypropylene, latex beads). Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The level of influenza B NS1 protein in a sample can be quantified and/or compared to controls. Suitable negative control samples are e.g. obtained from individuals known to be healthy, e.g., individuals known not to have an influenza viral infection. Specificity controls may be collected from individuals having known influenza A or influenza C infection, or individuals infected with viruses other than influenza. Control samples can be from individuals genetically related to the subject being tested, but can also be from genetically unrelated individuals. A suitable negative control sample can also be a sample collected from an individual at an earlier stage of infection, i.e., a time point earlier than the time point at which the test sample is taken. Recombinant NS1 of influenza B can be used as a positive control.

Western blots show that NS1 levels in biological samples are sufficient to allow detection of these antigens in a variety of different possible immunoassay formats. However, should the levels of NS1 in a particular biological sample prove to be limiting for detection in a particular immunoassay format, then, the live virus in a biological sample can be amplified by infecting cells in vitro, i.e., the NS1 protein in the virus-amplified sample should be detectable in about 6 hr to about 12 hr. The yield of NS1 antigen in biological samples and virus-amplified samples can also be improved by inclusion of protease inhibitors and proteasome inhibitors.

VII. Samples

Any biological sample from a subject can be used that contains or is thought might contain a detectable concentration of influenza proteins and preferably of NS1. For example, samples are often obtain from humans having or suspected of or at elevated risk of having influenza (e.g., through contact with others having influenza). Examples of samples that can be used are lung exudates, cell extracts (respiratory, epithelial lining nose), blood, mucous, and nasal swabs, for example. A high concentration of NS1 can be found in nasal swabs. Thus, a preferred sample for identification of NS1 is nasal secretion.

Binding of NS1 to an antibody occurs in the presence of up to 0.05% SDS, including 0.03% and 0.01%. Therefore, when the nasal or other bodily secretion is not likely to easily be used in a lateral flow format, it can be treated with SDS. Preferably, the amount of SDS added is up to a final concentration of 0.01%, more preferably 0.03% and even more preferably, 0.05%.

VIII. Diagnostic and Therapeutic Kits

Kits are provided for carrying out the present methods. The kits include one or more binding agents, typically antibodies or PDZ domains that specifically bind to NS1 of influenza A and/or B. The instant kit optionally contains one or more of the reagents, buffers or additive compositions or reagents disclosed in the examples. The kit can also include a means, such as a device or a system, for removing the influenza viral NS1 from other potential interfering substances in the biological sample. The instant kit can further include, if desired, one or more of various components useful in conducting an assay: e.g., one or more assay containers; one or more control or calibration reagents; one or more solid phase surfaces on which to conduct the assay; or, one or more buffers, additives or detection reagents or antibodies; one or more printed instructions detailing how to use the kit to detect influenza A and/or B, e.g. as package inserts and/or container labels, for indicating the quantities of the respective components that are to be used in performing the assay, as well as, guidelines for assessing the results of the assay. The instant kit can contain components useful for conducting a variety of different types of assay formats, including e.g. test strips, sandwich ELISA, Western blot assays, latex agglutination and the like.

IX. Antibody Arrays

The invention further provides arrays of antibodies and/or PDZ domains immobilized at different regions. Such arrays include a plurality of different antibodies and/or PDZ domains in different regions of the array, each with specificity for NS1 of influenza A and/or B. The different antibodies can be selected to have specificity for different subtypes and/or strains of influenza A and/or B. Antibodies that are panspecific for influenza A and/or B NS1 can also be included. Antibodies for influenza A or C NS1 proteins can also be included. Such arrays are useful for detection of influenza A and/or influenza B, and/or influenza C and distinguishing between subtypes and strains of these viruses.

Numerous formats for arrays have been proposed. U.S. Pat. No. 5,922,615 describes a device that utilizes multiple discrete zones of immobilized antibodies on membranes to detect multiple target antigens in an array. U.S. Pat. Nos. 5,458,852, 6,019,944, U.S. Pat. No. 6,143,576 and U.S. patent application Ser. No. 08/902,775 describe diagnostic devices with multiple discrete antibody zones immobilized in a device but not on a membrane for the assay of multiple target antigens. WO 99/67641 describes an array of microspheres is generated with tags that enable the decoding and identification of the specific binders (including antibodies) immobilized on individual microspheres after the microspheres are immobilized on the ends of optical fibers. In U.S. Pat. No. 5,981,180, microspheres are again used to immobilize binders (including antibodies) and the microspheres are distinguished from one another without separating them from the sample by detecting the relative amounts of two different fluorophores that are contained in the microspheres in order to identify the specific binder attached to the microsphere.

All publications, and patent filings cited in this specification are herein incorporated by reference as if each individual publication or patent were specifically and individually indicated to be incorporated by reference. Genbank records referenced by Genbank identification (GID) or accession number, particularly any polypeptide sequence, polynucleotide sequences or annotation thereof, are incorporated by reference herein. If more than one version of a sequence has been associated with the same accession number at different times, reference to a deposit number should be construed as applying to the version in existence at the effective filing date of the application dating back to a priority application if the deposit is also referenced in the priority application. Various changes may be made and equivalents may be substituted without departing from the true spirit and scope of the invention. For example, although the invention has been described primarily for influenza A and influenza B, a similar strategy can be used mutatis mutandis to detect influenza C. Unless otherwise apparent from the context, any feature, step or embodiment can be used in combination with any other feature, step or embodiment.

EXAMPLES

Example 1

NS1 Protein is Expressed in Human Clinical Specimens

Human nasal secretions were examined for the presence and amount of NS1 from Influenza A. Human nasal aspirates were collected and stored in M4 viral transport media (Remel, Inc, Lenexa, Kans.) at −80° C. Stored material was thawed and run on 10% SDS-PAGE. Western blot analysis was performed with monoclonal antibodies to NS1, 3H3 and 1A10 (Arbor Vita Corporation, Sunnyvale, Calif.). The results for six samples are shown in FIG. 4. The results show that NS1 is present in large amounts in nasal secretions.

To investigate the timeline of when NS1 was produced and secreted by cells infected with influenza A virus, MDCK cells were infected with human influenza A/PR/8 at a MOI of 0.1. Supernatant as well as cells were collected and lysed in 1% TRITON® X-100 and subjected to SDS-PAGE and western analysis with monoclonal antibody 3H3 which is pan-reactive to NS1. NS1 was detected in infected cells within 24 hours after infection and detected in the supernatant of infected cells within 48 hours (see FIG. 5). This suggests that a NS1 based diagnostic may be able to detect infection by influenza A within 48 hours and possibly within 24 hours.

Example 2

NS1 Interacts with PDZ in Cells

Figure 6:
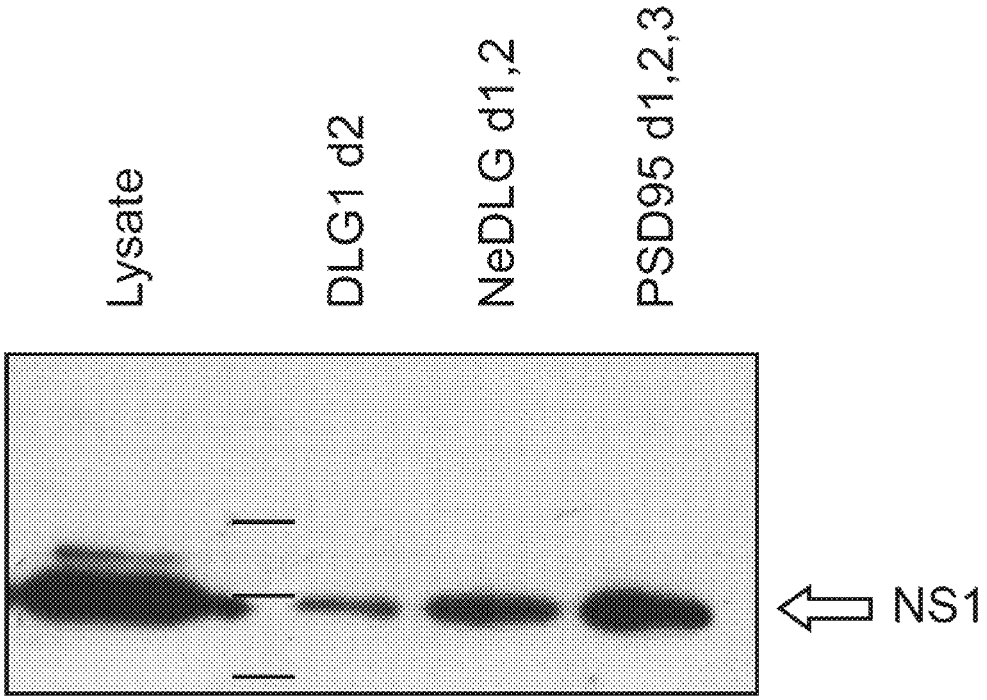
FIG. 6 shows that PDZ interacts with NS1 in cells.
Figure 7:
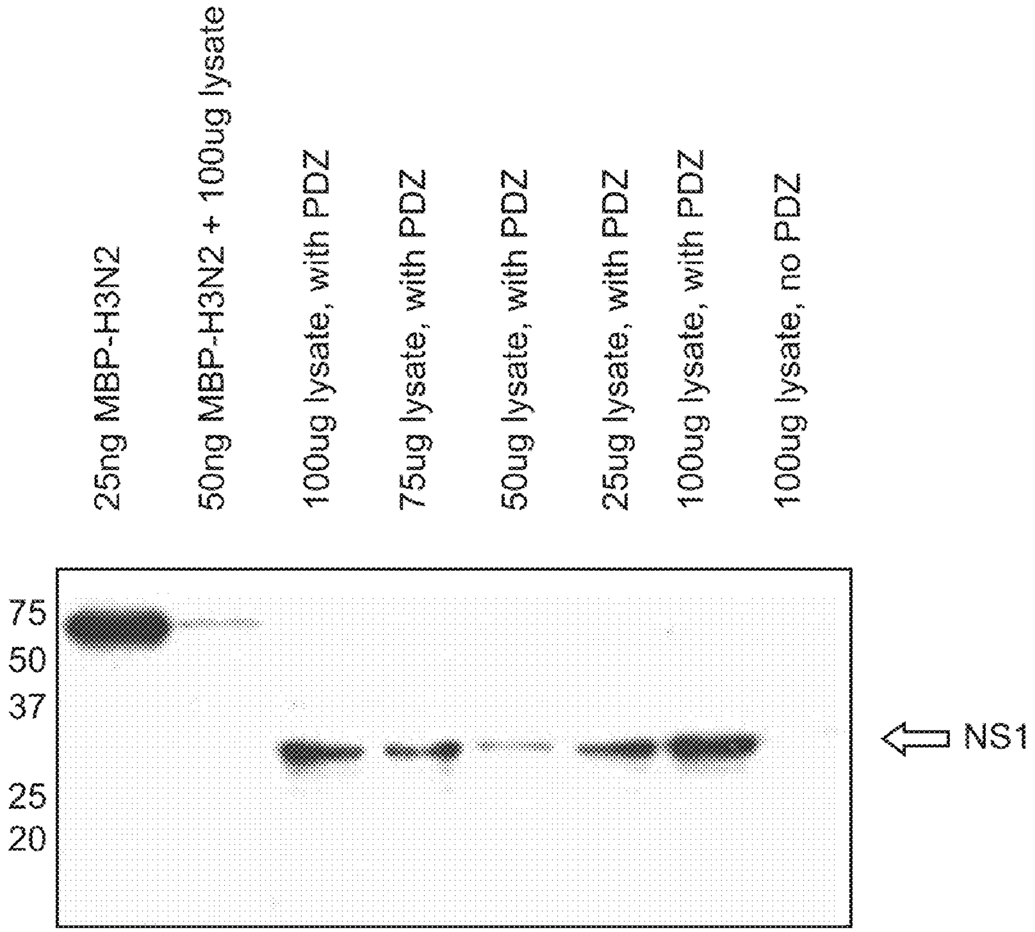
FIG. 7 shows that INADL d8 interacts with H3N2 NS1 in cells.

To verify that NS1 interacts with PDZ proteins in cells, a series of PDZ pull-down experiments were performed. 293 HEK cells were transfected with plasmids containing HA-NS1-H5N1B or with HA-NS1-H3N2. Lysates were prepared as described herein. Glutathione-SEPHAROSE -PDZ beads were prepared (10 ug of DLG1d1,2 10 ug of NeDLGd1, 2, and 10 ug PSD95d1,2,3) and used to pulldown 150 ug of lysate from transfected 293ET cells as shown in FIGS. 6 and 7. Following an overnight incubation at 4° C. and multiple washes with HNTG buffer, a membrane was prepared with the pulldowns. The membrane was probed with F63-3G1 supernatant (1:5). All 3 of the PDZs tested successfully pulldown NS1 from cell expressing HA-H5N1B (see FIG. 6).

Similarly, glutathione-SEPHAROSE-PDZ beads were prepared (40 ug of INADLd8) and used to pulldown 150 ug of lysate from 293ET cells transfected with H3N2. Following an overnight incubation at 4° C. and multiple washes with PBS, a western blot was prepared and probed a-HA (1:500) (Roche). INADL d8 successfully pulldown HA-H3N2 NS1 from cell lysate (FIG. 7).

The conclusion is that the NS1 PL is functional within the cell and can interact with PDZ domains as determined by the MATRIX assay.

Example 3

Monoclonal Antibodies to NS1

Monoclonal antibodies were prepared to specifically bind to subtype NS1 proteins (e.g., H5N1), NS1 PL classes (e.g., ESEV) and for pan-specificity (influenza A). The strategy for the generation of monoclonal antibodies to NS1 is as follows:

1. GST and MBP fusion proteins of NS1 were generated. The cloning vectors were obtained from Pharmacia (GST) or New England Biolabs (MBP). The NS1 coding regions were synthesized using overlapping oligonucleotides by DNA 2.0 (Menlo Park, Calif.).
2. Mice were immunized with MBP-NS1 fusion proteins at doses ranging from 10-100 ug per dose in CFA then IFA and PBS.
3. Splenocytes and lymphocytes were harvested 3 days after the last boost with the corresponding GST-NS1 fusion protein and fused with FOX-NY myeloma cells according to Kohler and Milstein (Nature 1975).
4. The hybridomas were screened first with MBP-NS1 in an ELISA. The positive wells were cloned and rescreened with a panel of MBP and GST NS1 and classified into pan-reactive or subtype reactive.
5. Further screenings were done using Western blots to verify the molecular weight of the target protein that is consistent with NS1.
6. An additional screening was performed using a S2 assay format (see Example 4) for compatibility with PDZ capture.
7. Steps 5 and 6 were repeated with eukaryotic expressed NS1 in the form of a cell lysate.
8. The antibodies are checked for compatibility with a lateral flow format described in Example 4.

Finally, the antibodies are checked for the ability to detect NS1 in a clinical specimen Example 4

Lateral Flow

Figure 8:
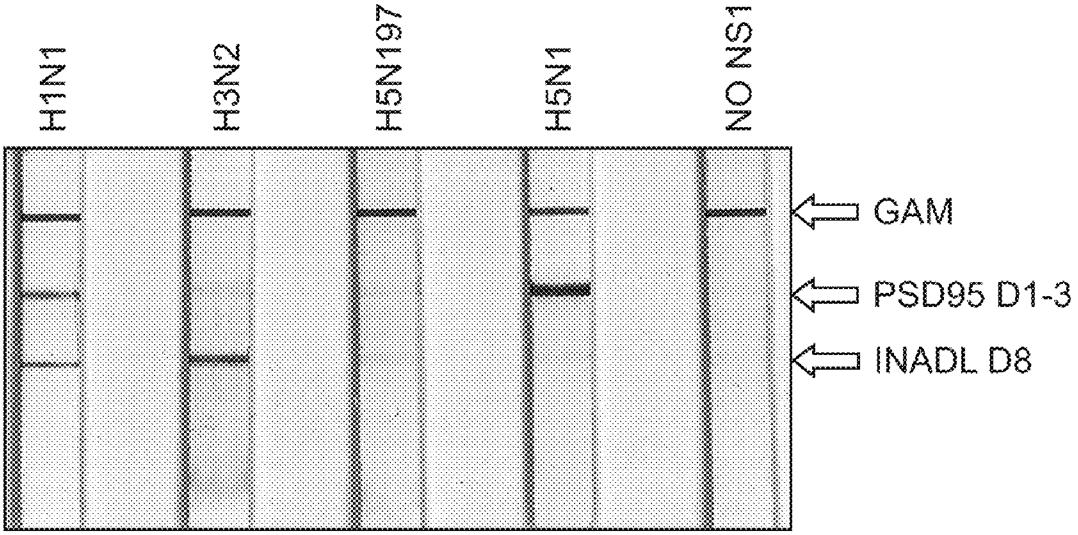
FIG. 8 shows a lateral flow format for an NS1 diagnostic using a PDZ capture agent and monoclonal antibody detect agent AU-4B2.

Examples of lateral flow formats for detection of NS1 are provided in FIGS. 8, 9 and 10A-F. FIG. 8 provides a lateral flow using PDZ capture followed by monoclonal antibody detection. For all cases, recombinant PDZ domain proteins or antibodies were deposited on RF120 Millipore membrane using a striper. For FIG. 8, the PDZ proteins PSD95D1-3, and INADL D8 were deposited at a concentration of 0.5 mg/ml. A control band was also deposited composed of goat anti-mouse antibody (GAM) also at 0.5 mg/ml. NS1 protein was combined with gold conjugated monoclonal anti-NS1 such as 4B2 in 100 ul volume in TBS-T buffer. The NS1 proteins used were from H1N1, H3N2, H5N197, H5N1, and a control lane did not contain NS1. In all cases, human nasal aspirates were diluted and stored in saline or M4, as indicated. The samples were directly mixed with gold conjugated antibody in the amounts described below.

The PDZ striped membrane was inserted into the NS1/anti-NS1 protein solution and flow initiated by capillary action and a wicking pad. NS1 was subtyped based on the pattern of PDZ reactivity; H1N1 binds to both PSD95 and INADL d8; H3N2 binds to INADL d8 only; H5N1 binds to PSD95 only. Influenza A subtyping was performed based on the results of the NS1 lateral flow using reactivity to PDZ and detection with a gold conjugated pan-reactive anti-NS1 monoclonal antibody.

Figure 9:
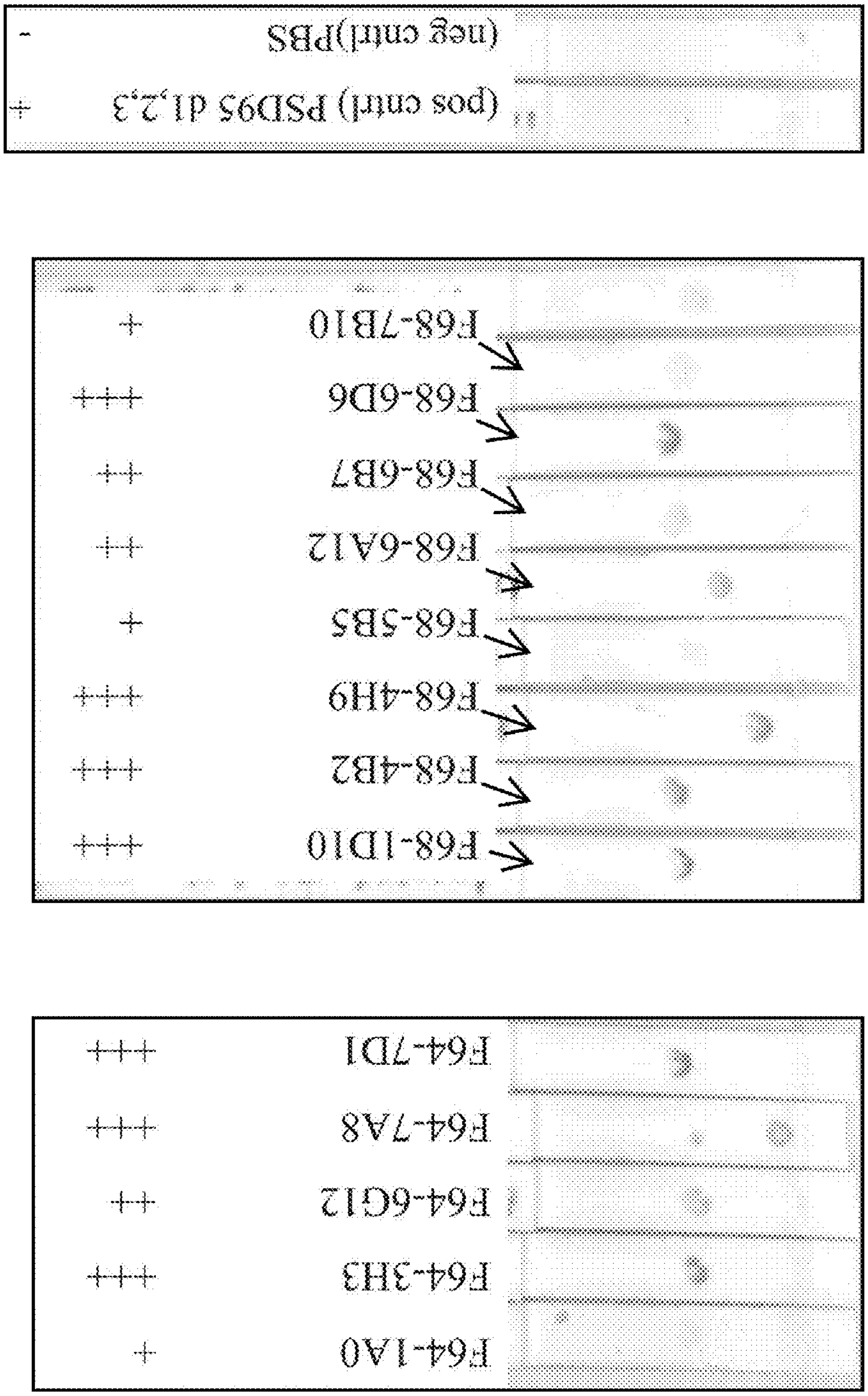
FIG. 9 shows a lateral flow format using a monoclonal antibody capture agent and a monoclonal antibody detect agent AU-4B2.

In FIG. 9, 13 different monoclonal antibodies were deposited on the lateral flow device. The 13 antibodies used were F64-1A0, F64-3H3, F64-6G12, F64-7A8, F64-7D1, F68-1D10, F68-4B2, F68-4H9, F68-6A12, F68-6B7, F68-6D6, F68-7B10. A subtype specific gold conjugated pan-NS1 antibody was added to a sample containing H1N1 influenza virus. The sample was applied to the lateral flow device and the results are shown in FIG. 9. The results show that a pan-specific antibody can be used for the test and the assay identified which antibodies were the best for binding to H1N1. The binding strength is quantified by using the following symbols: (−) for no binding, (+) for weak binding, (+++) for strong binding and (++) for moderate binding.

A lateral flow assay to identify pathogenic Influenza A in a patient sample is produced having pan-specific antibodies deposited on the membrane. The patient sample is admixed with a mixture of gold-labeled antibodies that recognize all NS1 PL's. The sample is applied to the lateral flow test strip and if a pathogenic strain of influenza A is present a line is formed on the strip.

The strip tests were run using the following protocol and materials: strips previously striped with goat anti-mouse/PSD95 d1,2,3/ INADL d8; TBST/ 2% BSA/ 0.25% TWEEN 20 buffer; Stocks of NS1 proteins MBP-H1N1, MBP-H3N2, MBP-H5N1A, and MBP-H5N1B "old" (Jon's) fast gold-conjugated F68-4B2 antibody; and Maxisorp ELISA plates.

The procedure was performed as follows:

1) Stock NS1 proteins were diluted down in TBST/ 2% BSA/ 0.25% TWEEN 20 to 100 ng/uL (using no less than 5uL of proteins to perform the dilutions)

2.) The 100 ng/uL dilution was diluted down to 50 ng/uL by adding 10 uL of the protein to 10 uL of TBST/ 2% BSA/ 0.25% Tween 20

3.) A stock solution of gold-conjugated antibody in TBST/ 2% BSA/ 0.25% TWEEN 20 buffer was prepared. Four uL of the antibody was added to every 100 uL of the buffer, and enough buffer was prepared for 6 100 uL reactions (which provides extra dead volume).

4.) 98 uL of the antibody/buffer mix was added to separate wells in the ELISA plate 5.) 2 uL of the NS1 dilutions were added to the buffer-containing wells (one NS1 per well)

6.) One well was left with just antibody and buffer to serve as a negative "no NS1" control 7.) The ELISA plate was tapped several times to mix the contents of the wells 8.) The pre-striped strips were added to the wells and observed during development.

After approximately 15 minutes (when all of the liquid had been absorbed, but the strip was not yet dry) the strips were removed from the wells and scanned into the computer.

The test provided in FIGS. 10A and 10B was prepared as follows: a GST-PSD95 d1,2,3 protein was striped onto the membrane at 3 mg/mL for the avian test, or alternatively a mixture of two monoclonal antibodies can be used (1.1 mg/mL F64-3H3 and 0.075 mg/mL F68-4H9 for the pan-flu A test. A second line of 1 mg/mL polyclonal goat anti-mouse antibody was used for the test capture line. The steps are set out below.

1. Prepare cards with a sample membrane and sink pad.

2. Stripe membrane with the PDZ protein and/or antibodies (see above for conc.)

3. Dry the membrane overnight at 56 degrees, then cut the cards into strips 4.26 mm wide.

4. Attach a glass fiber sample pad to the bottom of the strip and place the entire strip inside a cassette for testing.

5. Thaw sample to be tested and add 80 μl of sample to 20 μl of buffer. Pipette up and down several times to mix.

6. Spike 8 μl of the gold-conjugated (Au—) detector mix into the sample/buffer solution. This detector mix is 4 μl of Au-F68-4B2 with 4 μl of Au-F68-3D5. Pipette up and down several times to mix.

7. Add 100 μl of the prepared sample to the sample well on the cassette.

8. Read the test and control lines on the cassette at 15 minutes post-addition of sample. The control line is clearly visible for any test results to be read reliably. Flu A positive samples are noted with (+). Flu A negative samples are noted with (−). The top arrow is pointing to the control and the bottom arrow is pointing to the test. In both cases the top line is a control line (goat anti-mouse mAb), the second line down is the test line (mixture of F64-3H3 and F68-4H9 mAbs for the Pan-Flu A Test and PSD95 d1,2,3 for the Avian test). 2 ng of H5N1 protein was tested for the Avian test. The bottom circular spot is the sample well. In FIG. 10*a*, both test are positives.

Figure 10A:
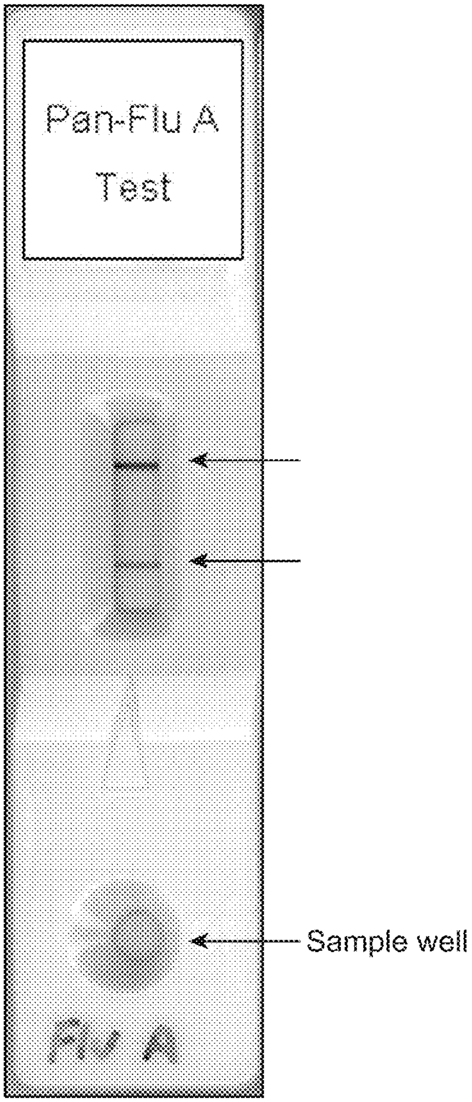
FIG. 10A-F exemplary lateral flow Influenza test formats.
Figure 10B:
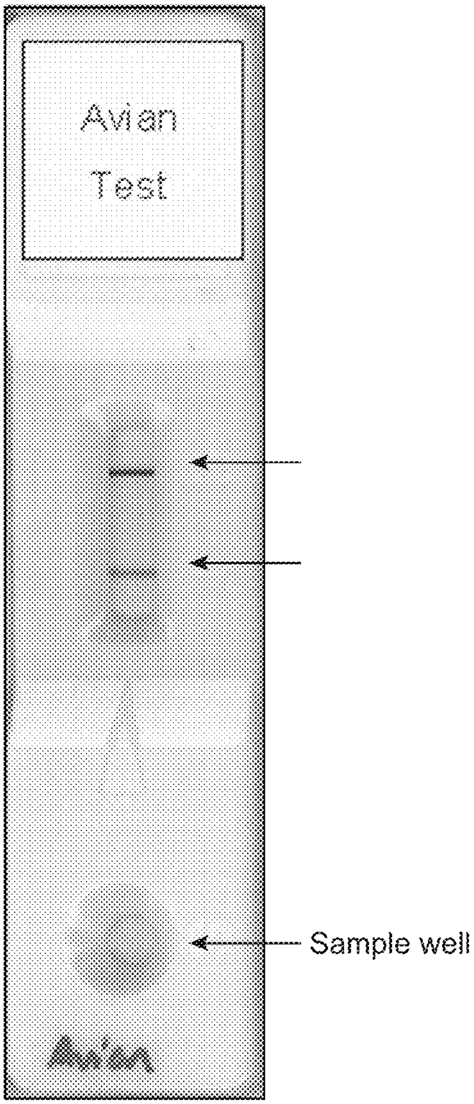
Figure 10C:
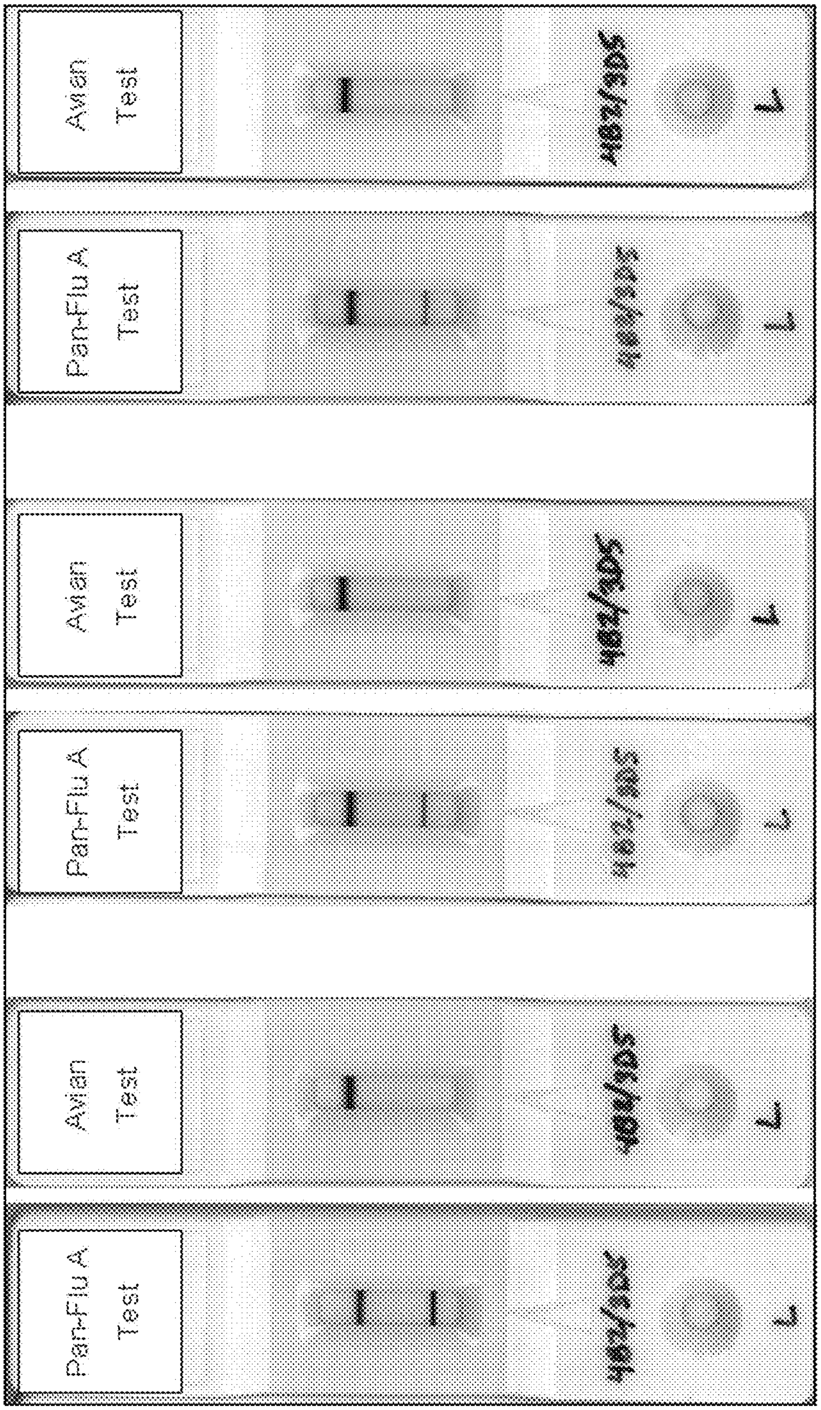
Figure 10D:
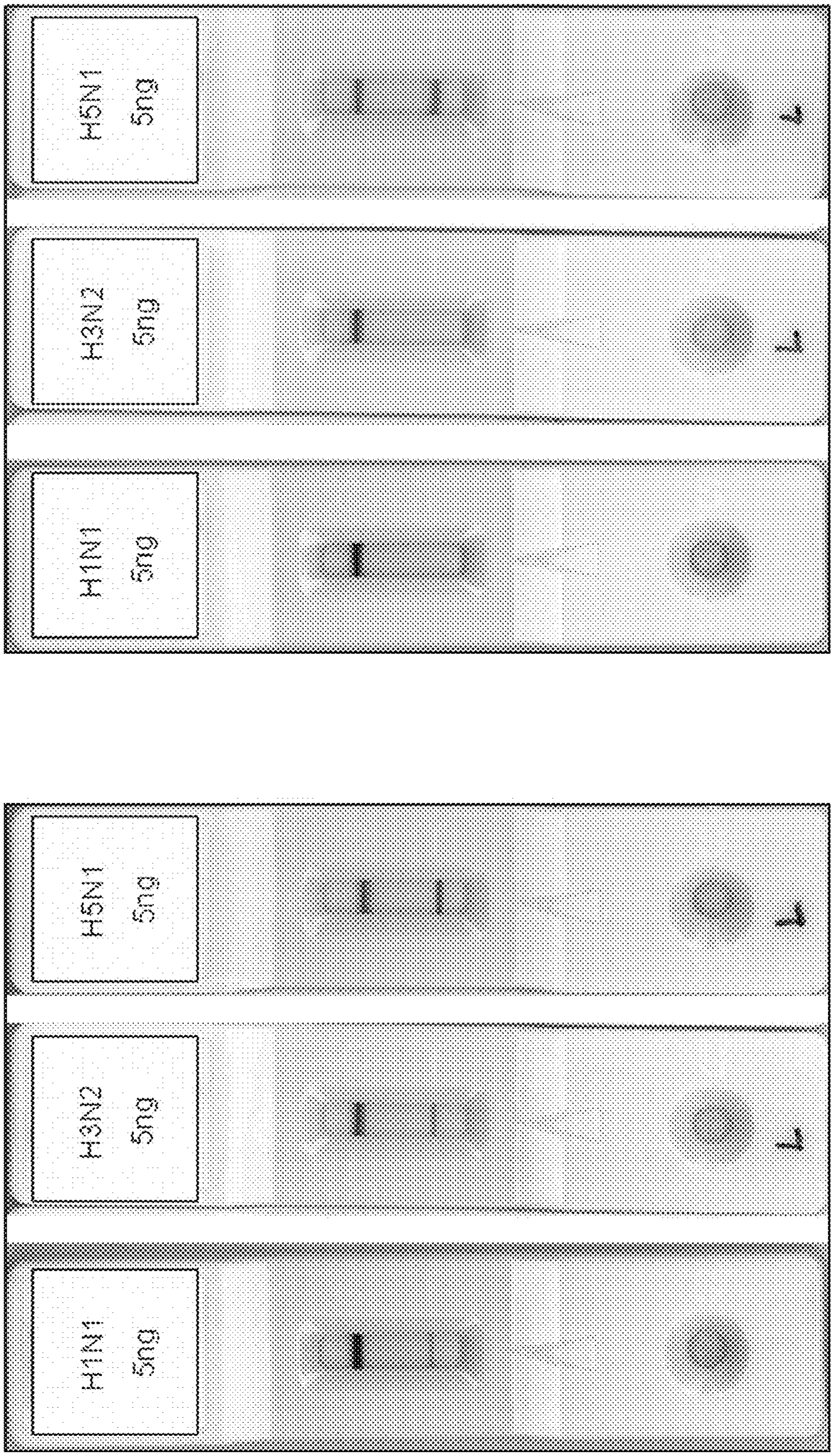

FIG. 10C shows three of twenty human samples that were tested with the format shown in FIGS. 10A and 10B. The samples showed a variety of outcomes, for example, Sample 1 was positive for Flu A, but negative for Avian Flu A (i.e., H5N1) and Sample 14 was negative for both (i.e., Flu A and H5N1). FIG. 10*d* shows the same test for H1N1, H3N2, and H5N1 recombinant proteins. The Pan-Flu A test was positive for all three. The Avian Flu test was positive for only H5N1.

Figure 10E:
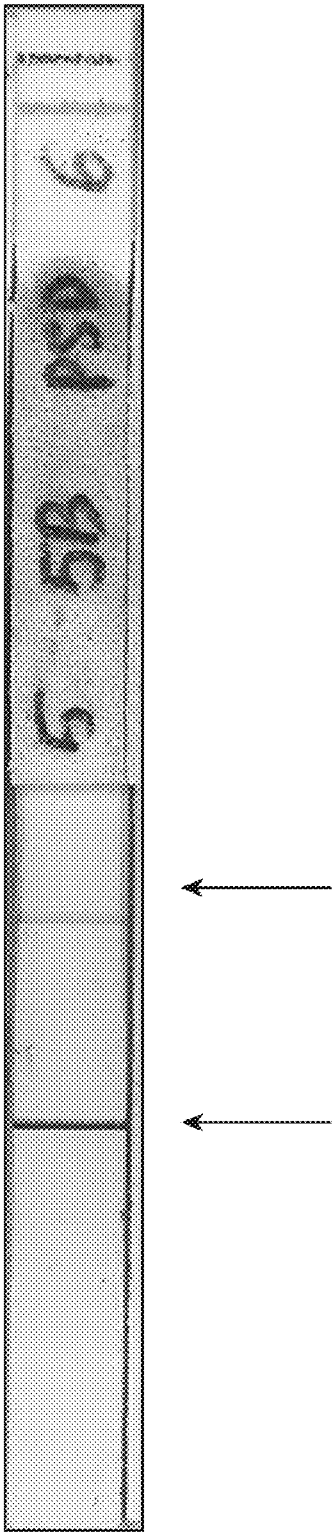

In FIG. 10E, Gold-conjugated PDZs were used as detectors and single or multiple mAbs were used for capture. FIG. 10E had liquid gold added in the form of Au-PSD95 d1,2,3 with a F68-4B2 mAb capture. 1.7 ng of NS1 H5N1 protein tested positively. This was an Avian Flu (i.e., H5N1) specific test.

Figure 10F:
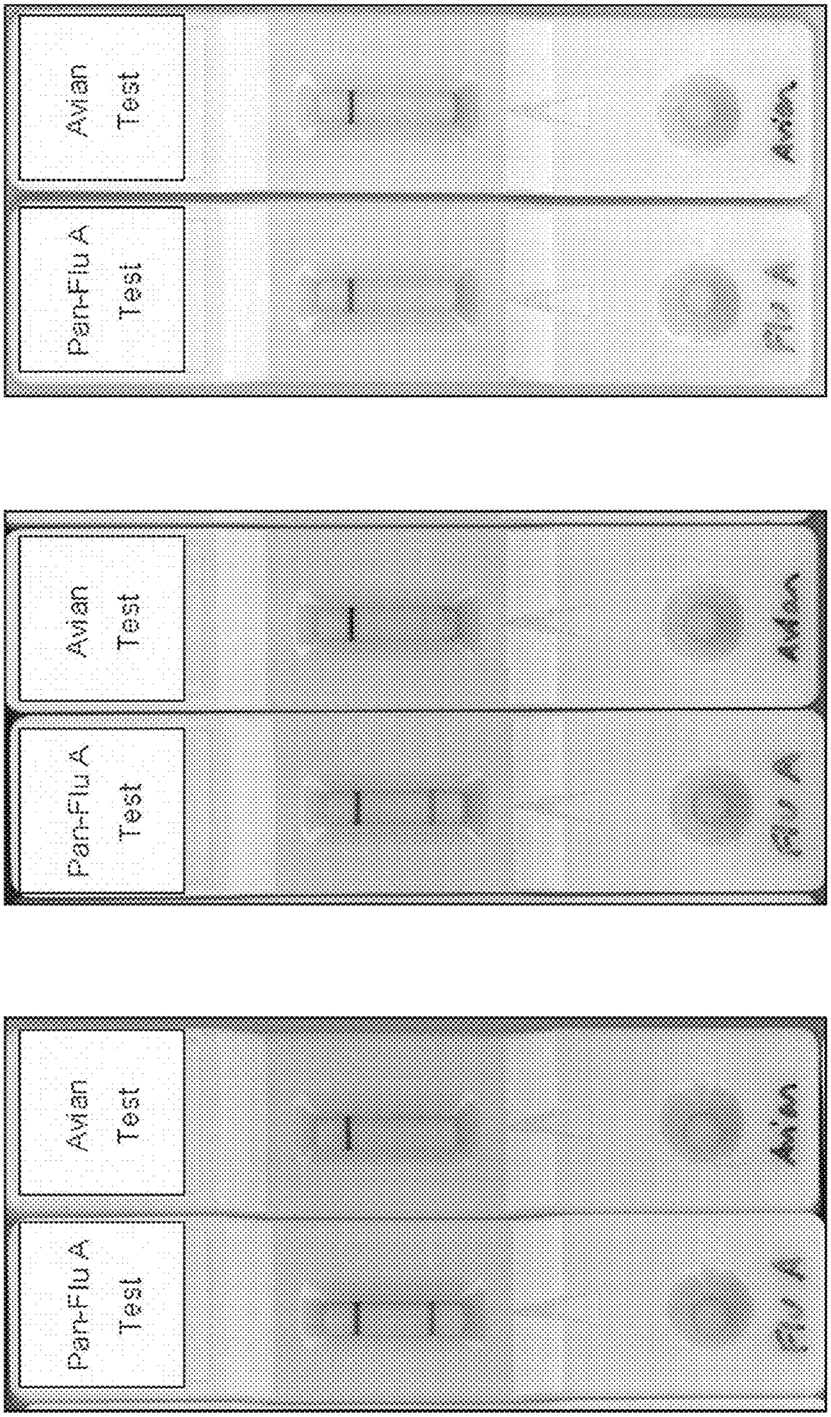

In FIG. 10F, a dried gold method was used. The cards were prepared as in the liquid gold protocol except the sample pad was affixed to the card before striping. When the captures were striped down, the gold-conjugated detector mix (which here also contained a conjugate diluent) was sprayed on the sample pad at the base of the card. The cards were dried, cut, and placed in cassettes as with the liquid test. When the human samples were prepared, they were treated with only the buffer solution before 100 μl was run on the cassette (no additional gold-conjugated detector mix was added). The Flu A positive samples are noted with a (+), the Flu A negative samples are noted with a (−). These cassettes were designed and read in the same way as the liquid gold cassettes. In FIG. 10F, Sample 7 and 9 were positive for both Flu A and Avian flu (i.e., H5N1) and sample 12 was negative for both Flu A and Avian flu (i.e., H5N1).

Example 5

Detection of Influenza B Using Panspecific Antibodies

Using anti-Influenza B NS1 monoclonal antibodies generated according to the above method, a lateral flow test was developed to detect Influenza B NS1. Monoclonal anti-influenza B NS1 antibodies were deposited on an HF075 Millipore membrane at a concentration of ~0.7 mg/ml using a striper. Some examples of antibodies deposited as capture agents are among the following: F89 1F4, F94 3A1, F89 4D5. A control band was also deposited composed of goat anti-mouse antibody (GAM) also at 1 mg/ml. Flu B NS1 protein was combined with gold conjugated monoclonal anti-NS1 such as F94 3A1 (when F94 3A1 is not used as capture) in 100 μl volume of AVC Flu B buffer. The Flu B NS1 proteins used were either recombinant AVC ID 522 (B/BA/78 NS1) and AVC ID 523 (B/YM/222/2002) or clinical samples of from patients known to be infected with influenza B.

The anti-Flu B NS1 antibody striped membrane was inserted into the Flu B NS1/anti-NS1 protein solution and flow initiated by capillary action and a wicking pad.

Several combinations of anti-Flu B NS1 capture and detection agents were used in several experiments. The following is an example protocol. The strip tests were run using strips previously striped with goat anti-mouse/F89 1F4 anti-Flu B NS1 monoclonal antibody; 90% M4 viral transport media, 10% of a 10×AVC Flu B buffer; Stocks of NS1 proteins MBP-Flu B NS1 (AVC 522 and AVC 523); gold conjugated F94 3A1 antibody; and Maxisorp ELISA plates. The procedure was performed as follows:

1) Stock NS1 proteins were diluted down in 90% M4 viral transport media, 10% of a 10×AVC Flu B buffer 9.) The stock of NS1 was diluted down to 0.5 ng/μL by diluting with 90% M4/10% of a 10×AVC Flu B buffer.

10.) Four μL of the gold-conjugated antibody was added to every 100 μL of the buffer 11.) 98 μL of the antibody/buffer mix was added to separate wells in the ELISA plate 12.) 2 μL of the NS1 dilutions were added to the buffer-containing wells (one NS1 per well) to achieve the desired final protein concentration (example 1 ng Flu B NS1)

13.) One well was left with just antibody and buffer to serve as a negative "no NS1" control 14.) The ELISA plate was tapped several times to mix the contents of the wells 15.) The pre-striped strips were added to the wells and observed during development.

After approximately 15 minutes (when all of the liquid had been absorbed, but the strip was not yet dry) the strips were removed from the wells and scanned into the computer.

Figure 11:
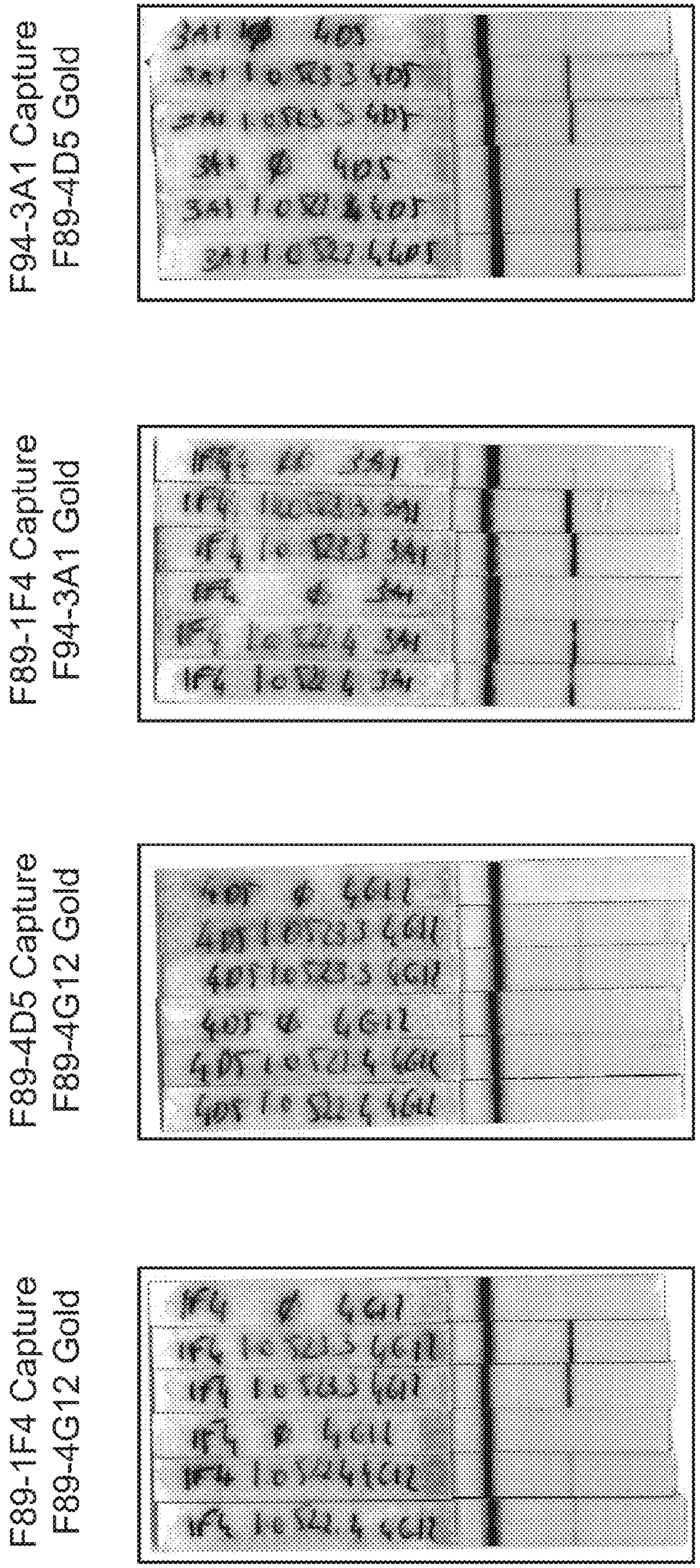
FIG. 11: Detection of recombinant NS1 from two strains of influenza B in a lateral flow assay using various combinations of capture and detection antibody.

FIG. 11 shows results from testing various pairs of monoclonal antibodies as capture and detection reagent on two strains of influenza B, B/BA78 (also known as strain 522), and B/Yagamata\222\2002, also known as strain 523). The four different panels show four combinations of antibodies. In each panel, tracks 3 and 6 are negative controls. Tracks 1 and 2 are recombinant NS1 from strain 522 and tracks 4 and 5 are recombinant NS1 from strain 523. The presence of additional bands in tracks 4 and 5 but not tracks 1 and 2 of the first panel shows that the F89-F4 capture antibody F89-4G12 detection antibody combination detects the 523 strain but does not detect the 522 strains. The other panels can be analyzed in the same way. The results from this experiment and other similar experiments are summarized in Table 13. Table 13 shows which antibodies can serve as a capture antibody and which as a detection antibody and whether the antibodies are panspecific for both strains of influenza B (522 and 523) or monospecific to 522 or 523. For example, the F89-1F4 antibody can serve as either a capture or detection antibody and is panspecific. F94-4C10 works as a detection antibody but not as a capture antibody and is specific for influenza B 523. F89-1F4 and F94-3A1 are preferred antibodies for use in lateral flow format.

Figure 12:
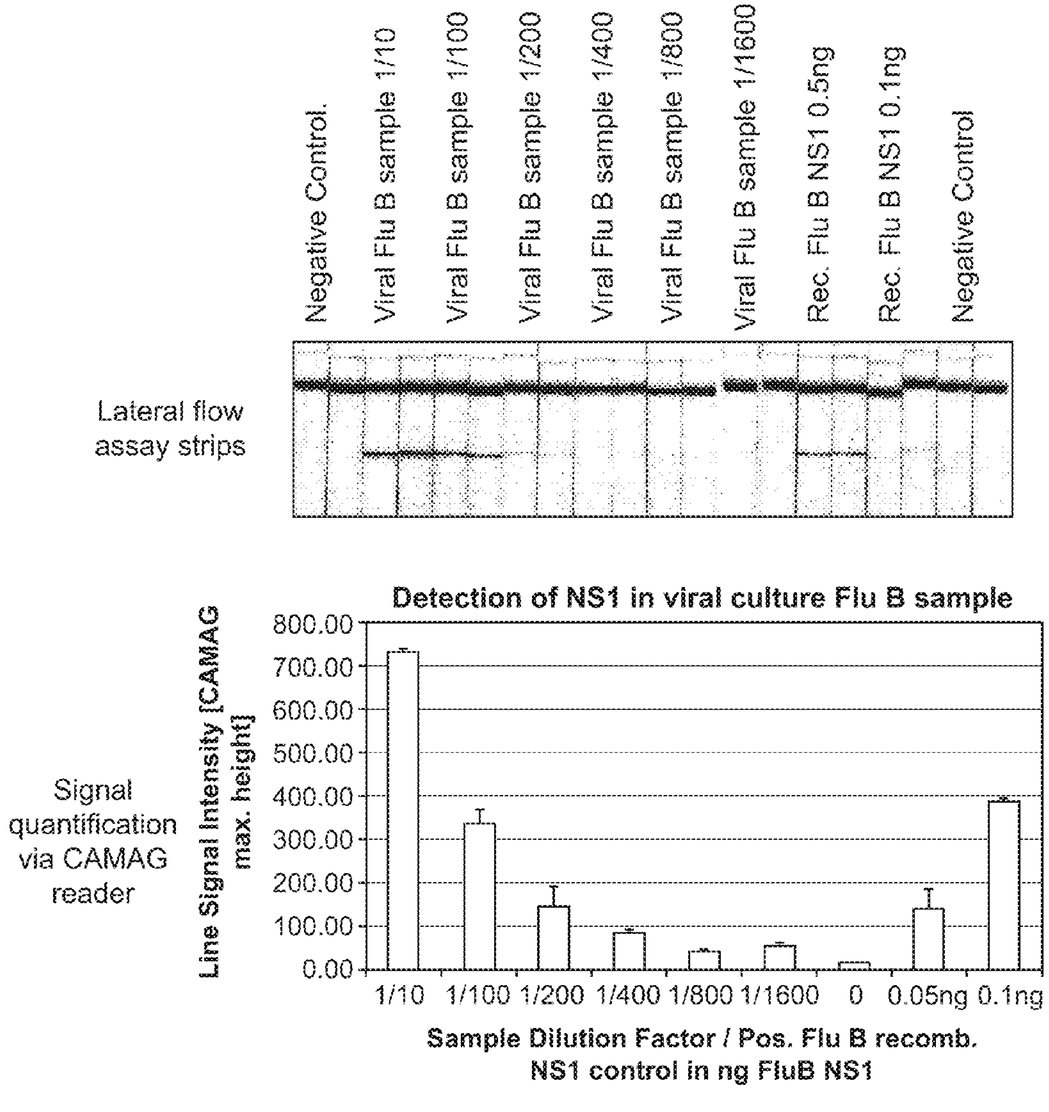
FIG. 12: Detection of NS1 from influenza B in clinical samples.

A lateral flow assay was used to identify Influenza B in a patient sample is produced having pan-specific antibodies deposited on the membrane. The patient sample was admixed with a mixture of gold-labeled antibodies that recognize all Influenza B NS1s. The sample was applied to the lateral flow test strip. Presence of influenza B is present a line is shown by a line formed on the strip. FIG. 12 shows the results from different dilutions of a patient sample compared with positive and negative controls. The upper part of the figure shows the actual appearance of lines indicating presence of influenza B. The lower part of the figure indicates the relative intensity of the bands. Influenza B was easily detectable up to a dilution of at least 400 fold.

What is claimed is:

1. A method of detecting influenza A, comprising:

(a) contacting a sample from a subject with a first agent comprising a PDZ domain that specifically binds to a PDZ-binding ligand sequence (PL) of an NS1 protein of a pathogenic subtype of influenza A;

(b) detecting presence or absence of specific binding of the first agent to any NS1 protein of a pathogenic influenza A in the sample wherein presence of specific binding to an NS1 protein indicates presence of the pathogenic influenza A subtype in the sample, and absence of specific binding to any NS1 protein indicates absence of the pathogenic influenza A subtype in the sample;

(c) contacting the patient sample with a second agent comprising a PDZ domain that specifically binds to a PL of an NS1 protein of a seasonal subtype of influenza A; and (d) detecting presence or absence of specific binding of the second agent to any NS1 protein of the seasonal subtype of influenza A in the sample wherein presence of specific binding to an NS1 protein indicates presence of the seasonal subtype of influenza A in the sample, and absence of specific binding to any NS1 protein indicates absence of the seasonal subtype of influenza A in the sample.

2. The method of claim 1, wherein the PDZ domain that specifically binds to the PL of an NS1 protein of a pathogenic subtype of influenza A is a PSD95 domain.

3. The method of claim 1, wherein the PDZ domain that specifically binds to the PL of an NS1 protein of a seasonal subtype of influenza A is an INADL domain.

4. The method of claim 1, wherein the sample is an orally obtained sample; a nasopharyngeal or oropharyngeal swab;

nasal lavage fluid; tissue from trachea, lungs, air sacs, sputum; water carrying biological materials; a cloacal swab; nasal mucus or oral mucus.

5. The method of claim 1, wherein the subject is a human showing symptoms of influenza.

6. The method of claim 2, wherein specific binding of the first agent comprising a PSD95 PDZ domain to any NS1 protein in the sample is detected by a sandwich assay in which the sample is contacted with an antibody that binds to the NS1 protein, and a complex of the PSD95 PDZ domain and the antibody both specifically bound to the NS1 protein is detected.

7. The method of claim 3, wherein specific binding of the second agent comprising an INADL PDZ domain to any NS1 protein is detected by a sandwich assay in which the sample is contacted with an antibody that binds to the NS1 protein, and a complex of the INADL PDZ domain and the antibody both specifically bound to the NS1 protein is detected.

8. The method of claim 2, wherein the first agent comprises a PDZ domain 2 of PSD95.

9. The method of claim 8, wherein the first agent comprises at least three copies of PSD95 domain 2.

10. The method of claim 2, wherein the first agent comprises domains 1, 2 and 3 of PSD95.

11. The method of claim 3, wherein the second agent comprises domain 8 of INADL.

12. The method of claim 1, wherein the second agent comprises three copies of domain 8 of INADL.

13. The method of claim 1, wherein detecting presence of specific binding of the PDZ domain in step (b) or (d) comprises detecting an extent of specific binding and the extent of specific binding is an indicator of the amount of the pathogenic (step b) or seasonal (step d) subtype of influenza A in the sample.

14. A method of detecting influenza A, comprising:

(a) contacting a sample from a subject with a first agent comprising a PDZ domain that specifically binds to a PDZ-binding ligand sequence (PL) of an NS1 protein of a pathogenic subtype of influenza A;

(b) contacting the patient sample with a second agent comprising a PDZ domain that specifically binds to a PL of an NS1 protein of a seasonal subtype of influenza A; and (c) detecting any NS-1 protein specific binding of the first and second agents;

wherein:

the PDZ domain that specifically binds to the PL of an NS1 protein of a pathogenic subtype of influenza A is a PSD95 domain;

the PDZ domain that specifically binds to the PL of an NS1 protein of a seasonal subtype of influenza A is an INADL domain 8;

and wherein:

(a) presence of NS1-specific binding of the PSD95 domain and absence of NS1-specific binding of the INADL domain 8, or greater NS1-specific binding of the PSD95 domain relative to NS1-specific binding of the INADL domain 8, is an indication the sample contains a pathogenic influenza A subtype; or (b) presence of NS1-specific binding of the INADL domain 8 and absence of NS1-specific binding of the PSD95 domain, or greater NS1-specific binding of the INADL domain relative to the NS1-specific binding of the PSD95 domain, is an indication the sample contains a seasonal influenza A subtype.

15. The method of claim 14, wherein the PSD95 domain is a PSD95 domain 2 and (a) presence of NS1-specific binding of the PSD95 domain 2 and relatively greater NS1-specific binding of the INADL domain compared with the PSD95 domain 2 is an indication that the sample contains a seasonal influenza A subtype H1N1, or (b) absence of NS1-specific binding of the PSD95 domain 2 combined with presence of specific binding of the INADL domain 8 is an indication that the sample contains a seasonal influenza A subtype H3N2.

16. The method of claim 14, wherein the subject is a human showing symptoms of influenza.

17. The method of claim 14, wherein detection is achieved using a lateral flow format.

18. The method of claim 1, wherein detection is achieved using a lateral flow format.

19. The method of claim 6, wherein detection is achieved using a lateral flow format.

20. The method of claim 14, wherein the pathogenic influenza A subtype is H5N1, or the seasonal influenza A subtype is H3N2 or H1N1.

21. The method of claim 20, wherein detection is achieved using a lateral flow format.

* * * * *

SEQUENCE LISTING

```
<160> NUMBER OF SEQ ID NOS: 10

<210> SEQ ID NO 1
<211> LENGTH: 230
<212> TYPE: PRT
<213> ORGANISM: Artificial
<220> FEATURE:
<223> OTHER INFORMATION: Invariant amino acid residues of NS1 from
      Influenza A subtypes H1N1, H3N2, and H5N1.
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (21)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (39)..(44)
<223> OTHER INFORMATION: Xaa can be any naturally occurring amino acid
<220> FEATURE:
<221> NAME/KEY: misc_feature
<222> LOCATION: (47)..(48)
<223> OTHER INFORMATION: Xaa can be any naturally occurring amino acid
<220> FEATURE:
```

-continued

```
<221> NAME/KEY: misc_feature
<222> LOCATION: (50)..(53)
<223> OTHER INFORMATION: Xaa can be any naturally occurring amino acid
<220> FEATURE:
<221> NAME/KEY: misc_feature
<222> LOCATION: (55)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (65)..(82)
<223> OTHER INFORMATION: Xaa can be any naturally occurring amino acid
<220> FEATURE:
<221> NAME/KEY: misc_feature
<222> LOCATION: (84)..(88)
<223> OTHER INFORMATION: Xaa can be any naturally occurring amino acid
<220> FEATURE:
<221> NAME/KEY: misc_feature
<222> LOCATION: (90)..(92)
<223> OTHER INFORMATION: Xaa can be any naturally occurring amino acid
<220> FEATURE:
<221> NAME/KEY: misc_feature
<222> LOCATION: (94)..(119)
<223> OTHER INFORMATION: Xaa can be any naturally occurring amino acid
<220> FEATURE:
<221> NAME/KEY: misc_feature
<222> LOCATION: (122)..(125)
<223> OTHER INFORMATION: Xaa can be any naturally occurring amino acid
<220> FEATURE:
<221> NAME/KEY: misc_feature
<222> LOCATION: (127)..(129)
<223> OTHER INFORMATION: Xaa can be any naturally occurring amino acid
<220> FEATURE:
<221> NAME/KEY: misc_feature
<222> LOCATION: (131)..(145)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (149)..(158)
<223> OTHER INFORMATION: Xaa can be any naturally occurring amino acid
<220> FEATURE:
<221> NAME/KEY: misc_feature
<222> LOCATION: (160)..(186)
<223> OTHER INFORMATION: Xaa can be any naturally occurring amino acid
<220> FEATURE:
<221> NAME/KEY: misc_feature
<222> LOCATION: (188)..(209)
<223> OTHER INFORMATION: Xaa can be any naturally occurring amino acid
<220> FEATURE:
<221> NAME/KEY: misc_feature
<222> LOCATION: (211)..(230)
<223> OTHER INFORMATION: Xaa can be any naturally occurring amino acid

<400> SEQUENCE: 1

Met Xaa Xaa Xaa Xaa Xaa Xaa Xaa Phe Gln Val Xaa Cys Phe Leu Trp
1               5                   10                  15

Xaa Xaa Arg Lys Xaa Xaa Xaa Xaa Xaa Xaa Xaa Xaa Asp Xaa Pro Phe
            20                  25                  30

Xaa Asp Arg Xaa Xaa Arg Xaa Xaa Xaa Xaa Xaa Xaa Gly Arg Xaa Xaa
        35                  40                  45

Thr Xaa Xaa Xaa Xaa Ile Xaa Xaa Xaa Xaa Xaa Xaa Gly Xaa Xaa Ile
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Ser Xaa Xaa Xaa Xaa Xaa Tyr Xaa Xaa Xaa Met Xaa Xaa Xaa
                85                  90                  95
```

-continued

```
Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Asp Gln Xaa Xaa Xaa Xaa Lys Xaa Xaa
        115                 120                 125

Xaa Leu Xaa Xaa Xaa Xaa Xaa Xaa Xaa Xaa Xaa Xaa Xaa Xaa Xaa Xaa
    130                 135                 140

Xaa Leu Xaa Arg Xaa Xaa Xaa Xaa Xaa Xaa Xaa Xaa Xaa Xaa Gly Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Glu Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Glu Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa
225                 230
```

```
<210> SEQ ID NO 2
<211> LENGTH: 230
<212> TYPE: PRT
<213> ORGANISM: Artificial
<220> FEATURE:
<223> OTHER INFORMATION: NS1 amino acid residues found in H5N1, but not
      H3N2 or H1N1.
<220> FEATURE:
<221> NAME/KEY: misc_feature
<222> LOCATION: (1)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(39)
<223> OTHER INFORMATION: Xaa can be any naturally occurring amino acid
<220> FEATURE:
<221> NAME/KEY: misc_feature
<222> LOCATION: (41)..(50)
<223> OTHER INFORMATION: Xaa can be any naturally occurring amino acid
<220> FEATURE:
<221> NAME/KEY: misc_feature
<222> LOCATION: (54)..(65)
<223> OTHER INFORMATION: Xaa can be any naturally occurring amino acid
<220> FEATURE:
<221> NAME/KEY: misc_feature
<222> LOCATION: (67)..(69)
<223> OTHER INFORMATION: Xaa can be any naturally occurring amino acid
<220> FEATURE:
<221> NAME/KEY: misc_feature
<222> LOCATION: (71)..(73)
```

-continued

```
<223> OTHER INFORMATION: Xaa can be any naturally occurring amino acid
<220> FEATURE:
<221> NAME/KEY: misc_feature
<222> LOCATION: (75)..(80)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(89)
<223> OTHER INFORMATION: Xaa can be any naturally occurring amino acid
<220> FEATURE:
<221> NAME/KEY: misc_feature
<222> LOCATION: (91)..(94)
<223> OTHER INFORMATION: Xaa can be any naturally occurring amino acid
<220> FEATURE:
<221> NAME/KEY: misc_feature
<222> LOCATION: (96)..(113)
<223> OTHER INFORMATION: Xaa can be any naturally occurring amino acid
<220> FEATURE:
<221> NAME/KEY: misc_feature
<222> LOCATION: (115)..(118)
<223> OTHER INFORMATION: Xaa can be any naturally occurring amino acid
<220> FEATURE:
<221> NAME/KEY: misc_feature
<222> LOCATION: (120)..(122)
<223> OTHER INFORMATION: Xaa can be any naturally occurring amino acid
<220> FEATURE:
<221> NAME/KEY: misc_feature
<222> LOCATION: (125)..(156)
<223> OTHER INFORMATION: Xaa can be any naturally occurring amino acid
<220> FEATURE:
<221> NAME/KEY: misc_feature
<222> LOCATION: (158)..(194)
<223> OTHER INFORMATION: Xaa can be any naturally occurring amino acid
<220> FEATURE:
<221> NAME/KEY: misc_feature
<222> LOCATION: (197)..(223)
<223> OTHER INFORMATION: Xaa can be any naturally occurring amino acid
<220> FEATURE:
<221> NAME/KEY: misc_feature
<222> LOCATION: (225)..(226)
<223> OTHER INFORMATION: Xaa can be any naturally occurring amino acid
<220> FEATURE:
<221> NAME/KEY: MISC_FEATURE
<222> LOCATION: (228)..(228)
<223> OTHER INFORMATION: X is serine or proline.

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Val Xaa Xaa Arg Phe Xaa Asp Xaa Glu Xaa Gly Xaa Ala Xaa Xaa
            20                  25                  30

Xaa Xaa Xaa Xaa Xaa Xaa Xaa Gln Xaa Xaa Xaa Xaa Xaa Xaa Xaa Xaa
        35                  40                  45

Xaa Xaa Gly Leu Asp Xaa Xaa Xaa Xaa Xaa Xaa Xaa Xaa Xaa Xaa Xaa
    50                  55                  60

Xaa Glu Xaa Xaa Xaa Glu Xaa Xaa Xaa Asp Xaa Xaa Xaa Xaa Xaa Xaa
65                  70                  75                  80

Ile Ala Xaa Val Xaa Xaa Xaa Xaa Xaa Leu Xaa Xaa Xaa Xaa Leu Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Ser Xaa Xaa Xaa Xaa Met Xaa Xaa Xaa Ile Met Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140
```

-continued

Xaa Xaa Xaa Xaa Xaa Xaa Xaa Xaa Xaa Xaa Xaa Xaa Arg Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Glu Asn Xaa Xaa Xaa Xaa Xaa Xaa Xaa Xaa Xaa Xaa Xaa Xaa
195 200 205

Xaa Xaa Xaa Xaa Xaa Xaa Xaa Xaa Xaa Xaa Xaa Xaa Xaa Xaa Xaa Arg
210 215 220

Xaa Xaa Glu Xaa Glu Val
225 230

<210> SEQ ID NO 3
<211> LENGTH: 234
<212> TYPE: PRT
<213> ORGANISM: Artificial
<220> FEATURE:
<223> OTHER INFORMATION: NS1 consensus sequence from Influenza A.

<400> SEQUENCE: 3

Met Asp Ser Asn Thr Val Leu Ser Phe Gln Val Asp Cys Phe Leu Trp
1 5 10 15

His Val Arg Lys Arg Phe Ala Asp Gln Glu Leu Gly Asp Ala Pro Phe
20 25 30

Leu Asp Arg Leu Arg Arg Asp Gln Lys Ser Leu Arg Gly Arg Gly Asn
35 40 45

Thr Leu Gly Leu Asp Ile Glu Thr Ala Thr Arg Ala Gly Lys Gln Ile
50 55 60

Val Glu Arg Ile Leu Glu Glu Glu Ser Asp Glu Ala Leu Lys Met Thr
65 70 75 80

Ile Ala Ser Val Pro Ala Ser Arg Tyr Leu Thr Asp Met Thr Leu Glu
85 90 95

Glu Met Ser Arg Asp Trp Phe Met Leu Met Pro Lys Gln Lys Val Ala
100 105 110

Gly Ser Leu Cys Ile Lys Met Asp Gln Ala Ile Met Asp Lys Thr Ile
115 120 125

Ile Leu Lys Ala Asn Phe Ser Val Ile Phe Asp Arg Leu Glu Thr Leu
130 135 140

Ile Leu Leu Arg Ala Phe Thr Glu Glu Gly Ala Ile Arg Val Gly Glu
145 150 155 160

Ile Ser Pro Leu Pro Ser Leu Pro Gly His Thr Gly Glu Asp Val Lys
165 170 175

Asn Ala Ile Gly Val Leu Ile Gly Gly Leu Glu Trp Asn Asp Asn Thr
180 185 190

Val Arg Val Ser Glu Asn Thr Ile Gln Arg Phe Ala Trp Arg Gly Ser
195 200 205

Asp Glu Asp Gly Arg Leu Pro Phe Pro Pro Asn Gln Lys Arg Lys Met
210 215 220

Ala Arg Thr Ile Glu Ser Glu Val Glu Lys
225 230

<210> SEQ ID NO 4
<211> LENGTH: 281
<212> TYPE: PRT
<213> ORGANISM: Artificial
<220> FEATURE:

-continued

<223> OTHER INFORMATION: NS1 consensus sequence from Influenza B.

<400> SEQUENCE: 4

```
Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asp Pro Ser Ala Gly
                85                  90                  95

Ile Glu Gly Phe Glu Pro Tyr Cys Met Lys Asn Pro Ser Asn Ser Asn
            100                 105                 110

Cys Pro Lys Cys Asn Trp Ala Asp Tyr Pro Leu Thr Pro Gly Lys Cys
        115                 120                 125

Leu Asp Asp Ile Glu Glu Glu Pro Glu Asp Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Leu Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Phe Asn Glu Gly His Pro Lys Pro Ile Arg
                245                 250                 255

Ala Ala Glu Thr Ala Met Gly Val Leu Ser Gln Phe Gly Gln Glu His
            260                 265                 270

Arg Leu Ser Pro Glu Glu Gly Asp Asn
        275                 280
```

<210> SEQ ID NO 5
<211> LENGTH: 10
<212> TYPE: PRT
<213> ORGANISM: Artificial
<220> FEATURE:
<223> OTHER INFORMATION: HA0 cleavage site sequence

<400> SEQUENCE: 5

```
Pro Glu Ile Pro Lys Gly Arg Gly Leu Phe
1               5                   10
```

<210> SEQ ID NO 6
<211> LENGTH: 10
<212> TYPE: PRT
<213> ORGANISM: Artificial
<220> FEATURE:
<223> OTHER INFORMATION: HA0 cleavage site sequence -continued

```
<400> SEQUENCE: 6

Pro Glu Asn Pro Lys Gly Arg Gly Leu Phe
1               5                   10


<210> SEQ ID NO 7
<211> LENGTH: 12
<212> TYPE: PRT
<213> ORGANISM: Artificial
<220> FEATURE:
<223> OTHER INFORMATION: HA0 cleavage site sequence

<400> SEQUENCE: 7

Pro Glu Ile Pro Lys Lys Lys Lys Arg Gly Leu Phe
1               5                   10


<210> SEQ ID NO 8
<211> LENGTH: 14
<212> TYPE: PRT
<213> ORGANISM: Artificial
<220> FEATURE:
<223> OTHER INFORMATION: HA0 cleavage site sequence

<400> SEQUENCE: 8

Pro Glu Thr Pro Lys Arg Lys Arg Lys Arg Gly Leu Ser Phe
1               5                   10


<210> SEQ ID NO 9
<211> LENGTH: 13
<212> TYPE: PRT
<213> ORGANISM: Artificial
<220> FEATURE:
<223> OTHER INFORMATION: HA0 cleavage site sequence

<400> SEQUENCE: 9

Pro Glu Ile Pro Lys Lys Arg Glu Lys Arg Gly Leu Phe
1               5                   10


<210> SEQ ID NO 10
<211> LENGTH: 12
<212> TYPE: PRT
<213> ORGANISM: Artificial
<220> FEATURE:
<223> OTHER INFORMATION: HA0 cleavage site sequence

<400> SEQUENCE: 10

Pro Glu Thr Pro Lys Arg Arg Arg Arg Gly Leu Phe
1               5                   10
```